US006590137B2

(12) United States Patent
Mitchell et al.

(10) Patent No.: US 6,590,137 B2

(45) **Date of Patent: *Jul. 8, 2003**

(54) MULTICOMPONENT SUPERABSORBENT GEL PARTICLES

(75) Inventors: Michael A. Mitchell, Lake Zurich, IL (US); Thomas W. Beihoffer, Arlington Heights, IL (US); Kimberly A. Rausch, Des Plaines, IL (US)

(73) Assignee: BASK Aktiengesellschaft, Ludwigshafen (DE)

(*) Notice: Subject to any disclaimer, the term of this patent is extended or adjusted under 35 U.S.C. 154(b) by 63 days.

This patent is subject to a terminal disclaimer.

(21) Appl. No.: 09/742,593

(22) Filed: Dec. 21, 2000

(65) Prior Publication Data

US 2001/0001312 A1 May 17, 2001

Related U.S. Application Data

(63) Continuation-in-part of application No. 09/179,553, filed on Oct. 28, 1998, now Pat. No. 6,222,091, which is a continuation of application No. 09/120,674, filed on Jul. 22, 1998, now Pat. No. 6,235,965, which is a continuation of application No. 08/974,125, filed on Nov. 19, 1998, now Pat. No. 6,072,101.

(51) Int. Cl.[7] .............................. A61F 13/15; C08L 8/00

(52) U.S. Cl. ....................... 604/372; 604/368; 525/191; 525/206; 525/218; 525/221; 525/178

(58) Field of Search ................................ 604/367, 368, 604/372; 525/178, 191, 206, 218, 221; 428/327, 402, 407

(56) References Cited

U.S. PATENT DOCUMENTS

| | | | |
|---|---|---|---|
| 3,041,292 A | 6/1962 | Hatch | 260/2.1 |
| 3,332,890 A | 7/1967 | Hatch | 260/2.1 |
| 3,645,922 A | 2/1972 | Weiss et al. | 260/2.1 R |

(List continued on next page.)

FOREIGN PATENT DOCUMENTS

| | | | |
|---|---|---|---|
| CA | 2066010 | 10/1992 | B01J/20/26 |
| DE | 43 33 056 | 3/1995 | C08F/8/00 |
| EP | 0 700 672 | 3/1996 | A61F/13/15 |
| WO | WO 95/22358 | 8/1995 | A61L/15/60 |
| WO | WO 96/15162 | 5/1996 | |
| WO | WO 96/15163 | 5/1996 | C08F/20/56 |
| WO | WO 96/15180 | 5/1996 | C08J/5/02 |
| WO | WO 96/17681 | 6/1996 | B01J/20/00 |
| WO | WO 98/37149 | 8/1998 | C08L/101/14 |
| WO | WO 98/24832 | 11/1998 | C08J/3/075 |

OTHER PUBLICATIONS

Bolto et al., Further Rapidly Reacting Ion–Exchange Resins, 1976, John Wiley & Sons, p. 87–94.*

Zhang et al., *Nature, 360*, 142–144 (1992).

Salamone et al., *Polym. Mater. Sci. Eng., 55*, 269–273 (1986)

(List continued on next page.)

*Primary Examiner*—Weilun Lo
*Assistant Examiner*—Michael J. Bogart
(74) *Attorney, Agent, or Firm*—Marshall, Gerstein & Borun

(57) ABSTRACT

Multicomponent superabsorbent gel particles are disclosed. The multicomponent particles comprise at least one acidic water-absorbing resin and at least one basic water-absorbing resin. Each particle contains about 20% to about 40%, by weight, of the basic resin, based on the total weight of the acidic resin and basic resin present in the particle. Blends of multicomponent superabsorbent gel particles with particles of a second water-absorbing resin also are disclosed. Improved diaper cores containing particles of the multicomponent superabsorbent gel particles also are disclosed.

39 Claims, 6 Drawing Sheets

14
12
10
16
16

U.S. PATENT DOCUMENTS 3,716,481 A 2/1973 Battaerd ...................... 210/32
3,758,641 A * 9/1973 Zweigle ...................... 260/874
3,901,236 A 8/1975 Assarsson ................... 128/284
3,957,698 A 5/1976 Hatch ...................... 260/2.1 R
4,139,499 A 2/1979 Wade et al. .................. 521/32
4,206,051 A 6/1980 Bolto et al. ................... 210/26
4,229,545 A 10/1980 Eppinger et al. ............. 521/38
4,378,439 A 3/1983 Pilkington ................... 521/26
4,578,068 A 3/1986 Kramer et al. .............. 604/368
4,685,909 A 8/1987 Berg et al. .................. 604/360
4,818,598 A 4/1989 Wong ......................... 428/284
5,026,800 A 6/1991 Kimura et al. .............. 526/200
5,075,399 A 12/1991 Ahmed et al. .............. 526/287
5,079,080 A 1/1992 Schwarz ..................... 428/288
5,085,787 A 2/1992 Pinschmidt, Jr. et al. 525/8.551
5,274,018 A 12/1993 Tanaka et al. .............. 524/166
5,340,865 A 8/1994 Neff et al. .................. 524/922
5,352,480 A * 10/1994 Hansen et al. .............. 427/202
5,384,343 A 1/1995 Farrar et al. ................ 524/556
5,409,771 A 4/1995 Dahmen et al. ............ 428/327
5,447,727 A 9/1995 Graham ...................... 424/487
5,547,745 A 8/1996 Hansen et al. .............. 428/283
5,643,662 A * 7/1997 Yeo et al. ................... 442/361
5,669,894 A 9/1997 Goldman et al. ........... 604/368
5,716,707 A 2/1998 Mukaida et al. ............ 428/402
5,763,523 A 6/1998 Chen et al. ................. 524/922
5,804,605 A 9/1998 Palumbo ...................... 521/28
5,849,862 A 12/1998 Davies et al. ........... 528/502 E
5,962,578 A * 10/1999 Beihoffer et al. ........... 524/521
6,072,101 A * 6/2000 Beihoffer et al. ........... 604/372
6,140,550 A * 10/2000 Beihoffer et al. ........... 604/366
6,156,020 A * 12/2000 Roe et al. .............. 604/385.01
6,159,591 A * 12/2000 Beihoffer et al. ........... 428/327
6,222,091 B1 * 4/2001 Beihoffer et al. ........... 604/368
6,235,965 B1 * 5/2001 Beihoffer et al. ........... 604/368
6,312,417 B1 * 11/2001 Hansson ................ 604/385.02
6,350,812 B1 * 2/2002 Vert et al. ................... 524/845
6,380,456 B1 * 4/2002 Goldman .................... 604/368

OTHER PUBLICATIONS

McCormick et al., *Macromolecules, 21*, 694–699 (1988).

Bolto, *Polymeric Amines and Ammonium Salts*, Goethals, Ed., Paragon Press, New York, p. 365 (1979).

Bolto et al., *J. Polymer Sci.: Symposium Ser., 55*, 95–104 (1976).

Badesso et al., *Hydrophilic Polymers; Performance with Environmental Acceptability*, Glass, Ed., American Chemical Society (1996).

St. Pierre et al., *Polym. Amines Ammonium Salts, Invited Lect. Contrib. Pap. Int. Symp.*, Goethals, Ed., p. 245 (1980), meeting date 1979.

Chang et al., *Macromolecules, 20*(3), 621–625 (1987).

Robeson, *J. App. Poly. Sci., 61*, 1561–1569 (1996).

* cited by examiner 0.28 AUL 3 hr
0.7 AUL 3 hr
AUNL 3 hr
48.9
Wt.% PVAm
0
10
20
30
40
50
60
70
80
90
100
110

MULTICOMPONENT SUPERABSORBENT GEL PARTICLES

CROSS REFERENCE TO RELATED APPLICATIONS

This is a continuation-in-part of U.S. patent application Ser. No. 09/179,553, filed Oct. 28, 1998, now U.S. Pat. No. 6,222,091, which is a continuation-in-part of U.S. patent application Ser. No. 09/120,674, filed Jul. 22, 1998, now U.S. Pat. No. 6,235,965, which is a continuation-in-part of U.S. patent application Ser. No. 08/974,125, filed Nov. 19, 1997, now U.S. Pat. No 6,072,101.

FIELD OF THE INVENTION

The present invention relates to multicomponent superabsorbent particles containing at least one acidic water-absorbing resin and at least one basic water-absorbing resin. Each superabsorbent particle contains about 20% to about 40% by weight of the basic resin, based on the total weight of the acidic resin and basic resin present in the particle. The present invention also relates to mixtures containing (a) multicomponent superabsorbent particles, and (b) particles of an acidic water-absorbing resin, a basic water-absorbing resin, or a mixture thereof.

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. Nos. 5,669,894 and 5,559,335, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used here and hereafter, the term "SAP particles" refers to superabsorbent polymer particles in the dry state, i.e., particles containing from no water up to an amount of water less than the weight of the particles. The terms "SAP gel" or "SAP hydrogel" refer to a superabsorbent polymer in the hydrated state, i.e., particles that have absorbed at least their weight in water, and typically several times their weight in water.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers function much less effectively in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi, 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, such as urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and salvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, such as urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

The removal of ions from electrolyte-containing solutions is often accomplished using ion exchange resins. In this process, deionization is performed by contacting an electrolyte-containing solution with two different types of ion exchange resins, i.e., an anion exchange resin and a cation exchange resin. The most common deionization procedure uses an acid resin (i.e., cation exchange) and a base resin (i.e., anion exchange). The two-step reaction for deionization is illustrated with respect to the desalinization of water as follows:

$$NaCl+R—SO_3H \rightarrow R—SO_3Na+HCl \quad HCl+R—N(CH_3)_3OH \rightarrow R—N(CH_3)_3Cl+H_2O.$$

The acid resin ($R—SO_3H$) removes the sodium ion; and the base resin ($R—N(CH_3)_3OH$) removes the chloride ions.

This ion exchange reaction, therefore, produces water as sodium chloride is adsorbed onto the resins. The resins used in ion exchange do not absorb significant amounts of water.

The most efficient ion exchange occurs when strong acid and strong base resins are employed. However, weak acid and weak base resins also can be used to deionize saline solutions. The efficiency of various combinations of acid and base exchange resins are as follows:

Strong acid—strong base (most efficient)

Weak acid—strong base

Strong acid—weak base

Weak acid—weak base (least efficient).

The weak acid/weak base resin combination requires that a "mixed bed" configuration be used to obtain deionization. The strong acid/strong base resin combination does not necessarily require a mixed bed configuration to deionize water. Deionization also can be achieved by sequentially passing the electrolyte-containing solution through a strong acid resin and strong base resin.

A "mixed bed" configuration of the prior art is a physical mixture of an acid ion exchange resin and a base ion exchange resin in an ion exchange column, as disclosed in Battaerd U.S. Pat. No. 3,716,481. Other patents directed to ion exchange resins having one ion exchange resin imbedded in a second ion exchange resin are Hatch U.S. Pat. No. 3,957,698, Wade et al. U.S. Pat. No. 4,139,499, Eppinger et al. U.S. Pat. No. 4,229,545, and Pilkington U.S. Pat. No. 4,378,439. Composite ion exchange resins also are disclosed in Hatch U.S. Pat. Nos. 3,041,092 and 3,332,890, and Weiss U.S. Pat. No. 3,645,922.

The above patents are directed to nonswelling resins that can be used to remove ions from aqueous fluids, and thereby provide purified water. Ion exchange resins used for water purification must not absorb significant amounts of water because resin swelling resulting from absorption can lead to bursting of the ion exchange containment column.

Ion exchange resins or fibers also have been disclosed for use in absorbent personal care devices (e.g., diapers) to control the pH of fluids that reach the skin, as set forth in Berg et al. U.S. Pat. No. 4,685,909. The ion exchange resin is used in this application to reduce diaper rash, but the ion exchange resin is not significantly water absorbent and, therefore, does not improve the absorption and retention properties of the diaper.

Ion exchange resins having a composite particle containing acid and base ion exchange particles embedded together in a matrix resin, or having acid and base ion exchange particles adjacent to one another in a particle that is free of a matrix resin are disclosed in B. A. Bolto et al., *J. Polymer Sci.:Symposium No.* 55, John Wiley and Sons, Inc. (1976), pages 87–94. The Bolto et al. publication is directed to improving the reaction rates of ion exchange resins for water purification and does not utilize resins that absorb substantial amounts of water.

Other investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, such as polyacrylic acid, and an amount of an ionizable surfactant sufficient to form at least a monolayer of surfactant on the polymer. In another embodiment, a cationic gel, such as a gel containing quaternized ammonium groups and in the hydroxide (i.e., OH) form, is admixed with an anionic gel (i.e., a polyacrylic acid) to remove electrolytes from the solution by ion exchange. Quaternized ammonium groups in the hydroxide form are very difficult and time-consuming to manufacture, thereby limiting the practical use of such cationic gels.

Wong U.S. Pat. No. 4,818,598 discloses the addition of a fibrous anion exchange material, such as DEAE (diethylaminoethyl) cellulose, to a hydrogel, such as a polyacrylate, to improve absorption properties. The ion exchange resin "pretreats" the saline solution (e.g., urine) as the solution flows through an absorbent structure (e.g., a diaper). This pretreatment removes a portion of the salt from the saline. The conventional SAP present in the absorbent structure then absorbs the treated saline more efficiently than untreated saline. The ion exchange resin, per se, does not absorb the saline solution, but merely helps overcome the "salt poisoning" effect.

WO 96/17681 discloses admixing discrete anionic SAP particles, such as polyacrylic acid, with discrete polysaccharide-based cationic SAP particles to overcome the salt poisoning effect. Similarly, WO 96/15163 discloses combining a cationic SAP having at least 20% of the functional groups in a basic (i.e., OH) form with a cationic exchange resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

These references disclose combinations that attempt to overcome the salt poisoning effect. However, the references merely teach the admixture of two types of particles, and do not suggest a single particle containing at least one microdomain of an acidic resin and at least one microdomain of a basic resin. These references also do not teach a mixture of resin particles wherein one component of the mixture is particles of a multicomponent SAP.

The present invention, therefore, is directed to discrete SAP particles containing a relatively low weight percent of a basic resin that exhibit exceptional water absorption and retention properties, especially with respect to electrolyte-containing liquids, and thereby overcome the salt poisoning effect. In addition, the discrete SAP particles have an ability to absorb liquids quickly, demonstrate good fluid permeability and conductivity into and through the SAP particle, and have a high gel strength such that the hydrogel formed from the SAP particles does not deform or flow under an applied stress or pressure, when used alone or in a mixture with other water-absorbing resins.

SUMMARY OF THE INVENTION

The present invention is directed to multicomponent SAPs comprising at least one acidic water-absorbing resin, such as a polyacrylic acid, and at least one basic water-absorbing resin, such as a poly(vinylamine) or a polyethyleneimine.

More particularly, the present invention is directed to multicomponent SAP particles containing at least one discrete microdomain of at least one acidic water-absorbing resin and at least one microdomain of at least one basic water-absorbing resin. The multicomponent SAP particles can contain a plurality of microdomains of the acidic water-absorbing resin and/or the basic water-absorbing resin dispersed throughout the particle. The acidic resin can be a strong or a weak acidic resin. Similarly, the basic resin can be a strong or a weak basic resin.

Each multicomponent SAP particle contains about 20% to about 40%, by weight, of the basic resin, based on the total weight of the acidic resin and basic resin present in the particle. A preferred SAP contains one or more microdomains of at least one weak acidic resin and one or more microdomains of at least one weak basic resin.

The properties demonstrated by such preferred multicomponent SAP particles are unexpected because, in ion exchange applications, the combination of a weak acid and a weak base is the least effective of any combination of a strong or weak acid ion exchange resin with a strong or weak basic ion exchange resin. Accordingly, one aspect of the present invention is to provide SAP particles that have a high absorption rate, have good permeability and gel strength, overcome the salt poisoning effect, and demonstrate an improved ability to absorb and retain electrolyte-containing liquids, such as saline, blood, urine, and menses. The present SAP particles contain discrete microdomains of acidic resin and basic resin, and during hydration, the particles resist coalescence but remain fluid permeable.

Another aspect of the present invention is to provide an SAP having improved absorption and retention properties compared to a conventional SAP, such as sodium polyacrylate. The present multicomponent SAP particles contain a low weight percentage of basic resin yet perform as well as multicomponent SAP particles containing a significantly higher weight percent of basic resin. The present multicomponent SAP particles therefore provide economies by utilizing less of an expensive basic resin, while exhibiting excellent absorption and retention properties.

The present multicomponent SAP particles are produced by any method that positions a microdomain of an acidic water-absorbing resin in contact with, or in close proximity to, a microdomain of a basic water-absorbing resin to provide a discrete particle. In one embodiment, the present SAP particles are produced by coextruding an acidic water-absorbing hydrogel and a basic water-absorbing hydrogel to provide multicomponent SAP particles having a plurality of discrete microdomains of an acidic resin and a basic resin dispersed throughout the particle, followed by heating the SAP particle for a sufficient time at a sufficient temperature to dry the multicomponent SAP particle. Such multicomponent SAP particles demonstrate improved absorption and retention properties, and improved permeability through and between particles compared to SAP compositions comprising a simple admixture of acidic resin particles and basic resin particles.

In another embodiment, the present multicomponent SAP particles can be prepared by admixing dry particles of a basic resin with a hydrogel of an acidic resin, then extruding the resulting mixture to form SAP particles having microdomains of a basic resin dispersed throughout a continuous phase of an acidic resin, followed by heating, i.e., annealing, the SAP particles. Alternatively, dry acidic resin particles can be admixed with a basic resin hydrogel, followed by extruding the resulting mixture to form multicomponent SAP particles having microdomains of an acidic resin dispersed in a continuous phase of a basic resin, then heating the SAP particles.

In addition, a multicomponent SAP particle containing microdomains of an acidic resin and a basic resin dispersed in a continuous phase of a matrix resin can be prepared by adding dry particles of the acidic resin and dry particles of the basic resin to a hydrogel of the matrix hydrogel, then extruding and heating. Other forms of the present multicomponent SAP particles, such as agglomerated particles, interpenetrating polymer network forms, laminar forms, and concentric sphere forms, also demonstrate improved fluid absorption and retention properties.

In other important embodiments, the acidic and basic water-absorbing hydrogels are coextruded, or spun, to form a fiber having a core-sheath configuration. Alternatively, the acidic and basic water-absorbing hydrogels are extruded, or spun, individually, then twisted together, in the form of a braid, to provide a multicomponent SAP fiber.

In accordance with yet another important aspect of the present invention, the acidic and basic resins are lightly crosslinked, such as with a suitable polyfunctional vinyl polymer. In preferred embodiments, the acidic resin, the basic resin, and/or the entire multicomponent SAP particle are surface treated to further improve water absorption and retention properties, especially under a load.

Yet another important feature of the present invention is to provide a multicomponent SAP particle containing about 60% to about 80%, by weight, of a weak acidic water-absorbing resin and about 20% to about 40%, by weight, of a weak basic water-absorbing resin, based on the total weight of the acidic and basic resin.

An example of a weak acidic resin is polyacrylic acid having 0% to 25% neutralized carboxylic acid groups (i.e., DN=0 to DN=25). Examples of weak basic water-absorbing resins are a poly(vinylamine) and a polyethylenimine. Examples of a strong basic water-absorbing resin are poly(vinylguanidine) and poly(allylguanidine).

Yet another aspect of the present invention is to provide an improved SAP material comprising a combination containing (a) multicomponent SAP particles, and (b) particles of a second water-absorbing resin selected from the group consisting of an acidic water-absorbing resin, a basic water-absorbing resin, and a mixture thereof. The combination contains about 10% to about 90%, by weight, multicomponent SAP particles and about 10% to about 90%, by weight, particles of the second water-absorbing resin.

Still another aspect of the present invention is to provide articles of manufacture, like diapers and catamenial devices, having a core comprising multicomponent SAP particles or an SAP material of the present invention. Other articles that can contain the multicomponent SAP particles or an SAP material of the present invention include adult incontinence products, and devices for absorbing saline and other ion-containing fluids.

These and other aspects and advantages of the present invention will become apparent from the following detailed description of the preferred embodiments.

DETAILED DESCRIPTION OF THE PREFERRED EMBODIMENTS

The present invention is directed to multicomponent SAP particles containing at least one microdomain of an acidic water-absorbing resin and at least one microdomain of a basic water-absorbing resin. Each particle contains one or more microdomains of an acidic resin and one or more microdomains of a basic resin. The basic resin is present in each particle in an amount of about 20% to about 40%, by weight, based on the total weight of acidic resin and basic resin in the particle. The microdomains can be distributed nonhomogeneously or homogeneously throughout each particle.

Each multicomponent SAP particle of the present invention contains at least one acidic water-absorbing resin and at least one basic water-absorbing resin. In one embodiment, the SAP particles consist essentially of acidic resins and basic resins, and contain microdomains of the acidic and/or basic resins. In another embodiment, microdomains of the acidic and basic resins are dispersed in an absorbent matrix resin.

The multicomponent SAP particles of the present invention are not limited to a particular structure or shape. However, it is important that substantially each SAP particle contain at least one microdomain of an acidic water-absorbing resin and at least one microdomain of a basic water-absorbing resin. Improved water absorption and retention, and improved fluid permeability through and between SAP particles, are observed when the acidic resin microdomain and the basic resin microdomain are in contact with one another.

In some embodiments, an idealized multicomponent SAP particle of the present invention is analogous to a liquid emulsion wherein small droplets of a first liquid, i.e., the dispersed phase, are dispersed in a second liquid, i.e., the continuous phase. The first and second liquids are immiscible, and the first liquid, therefore, is homogeneously dispersed in the second liquid. The first liquid can be water or oil based, and conversely, the second liquid is oil or water based, respectively.

Figure 1:
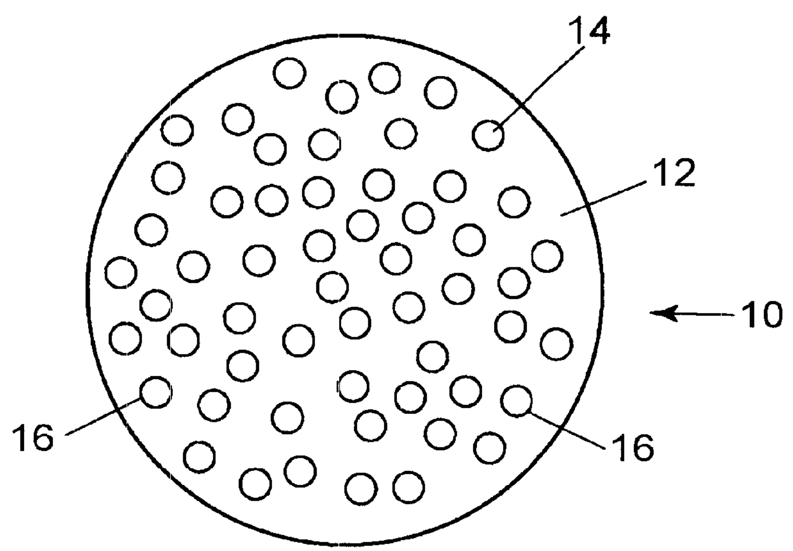
FIG. 1 is a schematic diagram of a water-absorbing particle containing microdomains of a first resin dispersed in, and covalently bound to, a continuous phase of a second resin.

Therefore, in one embodiment, the multicomponent SAP particles of the present invention can be envisioned as one or more microdomains of an acidic resin dispersed in a continuous phase of a basic resin, or as one or more microdomains of a basic resin dispersed in a continuous acid resin. These idealized multicomponent SAP particles are illustrated in FIG. 1 showing an SAP particle 10 having discrete microdomains 14 of a dispersed resin in a continuous phase of a second resin 12. If microdomains 14 comprise an acidic resin, then continuous phase 12 comprises a basic resin. Conversely, if microdomains 14 comprise a basic resin, then continuous phase 12 is an acidic resin.

Figure 2:
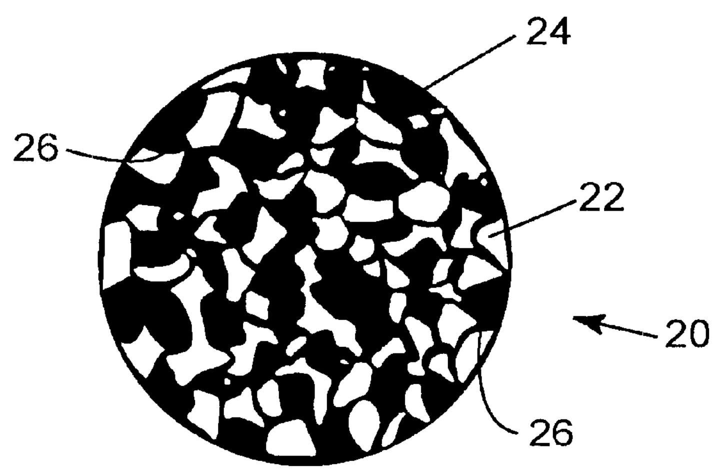
FIG. 2 is a schematic diagram of a water-absorbing particle containing microdomains of a first resin and microdomains of a second resin dispersed throughout the particle.

In another embodiment, the SAP particles are envisioned as microdomains of an acidic resin and microdomains of a basic resin dispersed throughout each particle, without a continuous phase. This embodiment is illustrated in FIG. 2, showing an idealized multicomponent SAP particle 20 having a plurality of microdomains of an acidic resin 22 and a plurality of microdomains of a basic resin 24 dispersed throughout particle 20.

In yet another embodiment, microdomains of the acidic and basic resins are dispersed throughout a continuous phase comprising a matrix resin. This embodiment also is illustrated in FIG. 1 wherein multicomponent SAP particle 10 contains one or more microdomains 14, each an acidic resin or a basic resin, dispersed in a continuous phase 12 of a matrix resin.

Figure 3A:
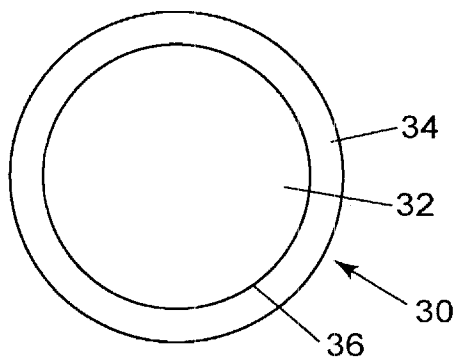
FIGS. 3A and 3B are schematic diagrams of a water-absorbing particle having a core microdomain of a first resin surrounded by a layer of a second resin.

It should be understood that the microdomains within each particle can be of regular or irregular shape, and that the microdomains can be dispersed homogeneously or nonhomogeneously throughout each particle. Accordingly, another embodiment of the SAP particles is illustrated in FIG. 3A, showing an idealized multicomponent particle 30 having a core 32 of an acidic water-absorbing resin surrounded by a shell 34 of a basic water-absorbing resin. Conversely, core 32 can comprise a basic resin, and shell 34 can comprise an acidic resin.

Figure 3B:
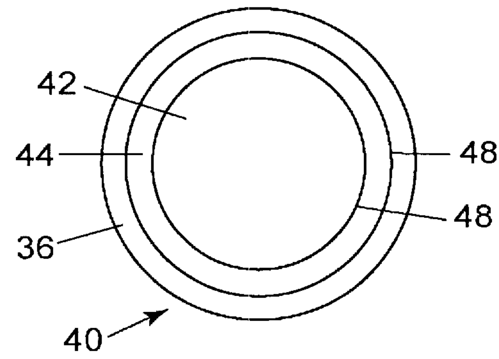

FIG. 3B illustrates a similar embodiment, i.e., an idealized multicomponent particle 40, having a core and concentric shells that alternate between shells of acidic resin and basic resin. In one embodiment, core 42 and shell 46 comprise an acidic water-absorbing resin, and shell 44 comprises a basic water-absorbing resin. Other embodiments include: core 42 and shell 46 comprising a basic resin and shell 44 comprising an acidic resin, or core 42 comprising a matrix resin and shells 44 and 46 comprising an acidic resin and a basic resin in alternating shells. Other configurations are apparent to persons skilled in the art, such as increasing the number of shells around the core.

Figure 4A:
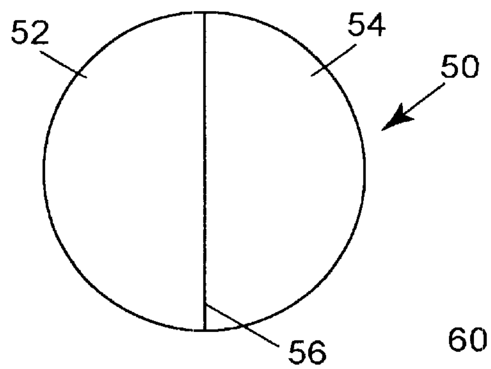
FIGS. 4A–D are schematic diagrams of water-absorbing particles having a microdomain of a first resin and a microdomain of a second resin.
Figure 4B:
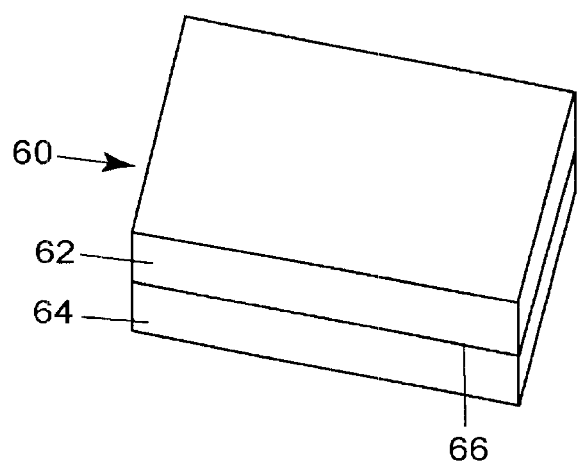
Figure 4C:
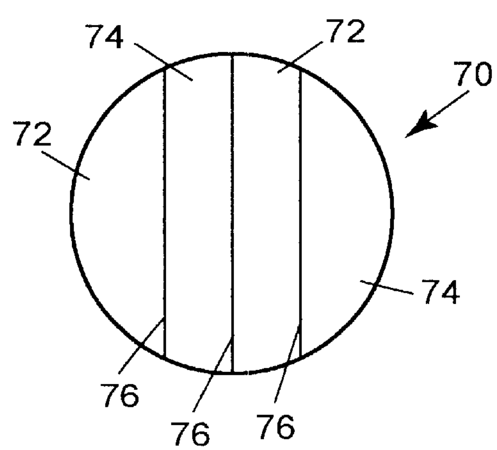
Figure 4D:
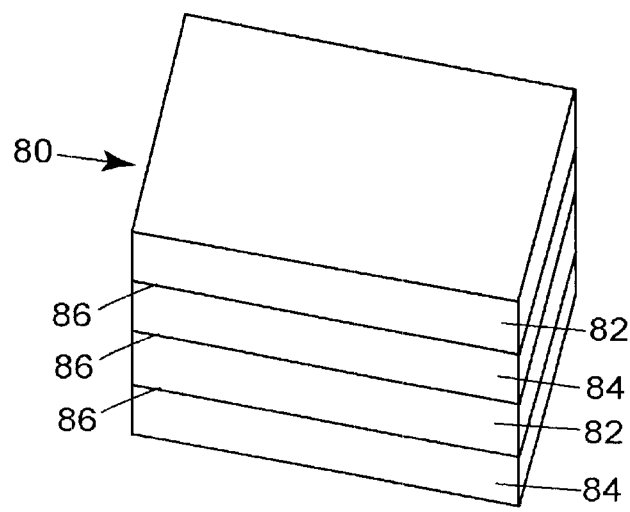

FIGS. 4A and 4B illustrate embodiments of the present SAP particles wherein one microdomain of an acidic water-absorbing resin (i.e., 52 or 62) is in contact with one microdomain of a basic water-absorbing resin (i.e., 54 or 64) at an interface (i.e., 56 or 66) to provide a multicomponent SAP particle (i.e., 50 or 60). In these embodiments, the microdomains are dispersed nonhomogeneously throughout the particle. The embodiments illustrated in FIG. 4 extend to SAP particles having more than one microdomain of each of the acidic resin and the basic resin, as illustrated in FIGS. 4C and 4D, wherein multicomponent SAP particles 70 and 80 contain alternating zones of acidic water-absorbing resin (e.g., 72 or 82) and basic water-absorbing resin (e.g., 74 or 84) in contact at interfaces 76 or 86. Particles 70 and 80 also can contain one or more layers 72, 74, 82, or 84 comprising a matrix resin.

In another embodiment, the multicomponent SAP particle comprises an interpenetrating polymer network (IPN), as illustrated in FIG. 5. An IPN is a material containing two polymers, each in network form. In an IPN, two polymers are synthesized and/or crosslinked in the presence of one another, and polymerization can be sequential or simultaneous. Preparation of a sequential IPN begins with the synthesis of a first crosslinked polymer. Then, monomers comprising a second polymer, a crosslinker, and initiator are swollen into the first polymer, and polymerized and crosslinked in situ. For example, a crosslinked poly(acrylic acid) network can be infused with solution containing a poly(vinylamine) and a crosslinker.

Simultaneous IPNs are prepared using a solution containing monomers of both polymers and their respective crosslinkers, which then are polymerized simultaneously by noninterfering modes, such as stepwise or chain polymerizations. A third method of synthesizing IPNs utilizes two lattices of linear polymers, mixing and coagulating the lattices, and crosslinking the two components simultaneously. Persons skilled in the art are aware of other ways that an IPN can be prepared, each yielding a particular topology.

In most IPNs, the polymer phases separate to form distinct zones of the first polymer and distinct zones of the second polymer. In the IPNs, the first and second polymers remain "soluble" in one another. Both forms of IPN have microdomains, and are multicomponent SAPs of the present invention.

Figure 5A:
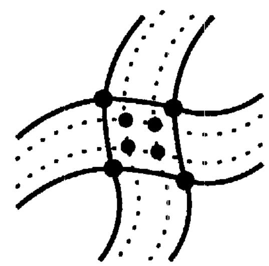
FIGS. 5A and 5B are schematic diagrams of a water-absorbing particle having an interpenetrating network of a first resin and a second resin.
Figure 5B:
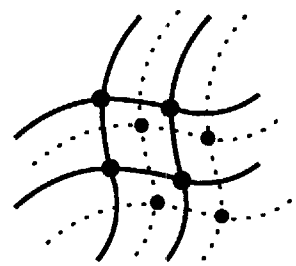

FIGS. 5A and 5B illustrate IPN systems. FIG. 5A illustrates an IPN made by sequentially synthesizing the first and second polymers. FIG. 5B illustrates an IPN made by simultaneously polymerizing the first and second polymers. In FIGS. 5A and 5B, the solid lines represent the first polymer (e.g., the acidic polymer) and the lightly dotted lines represent the second polymer (e.g., the basic polymer). The heavy dots represent crosslinking sites.

Figure 6A:
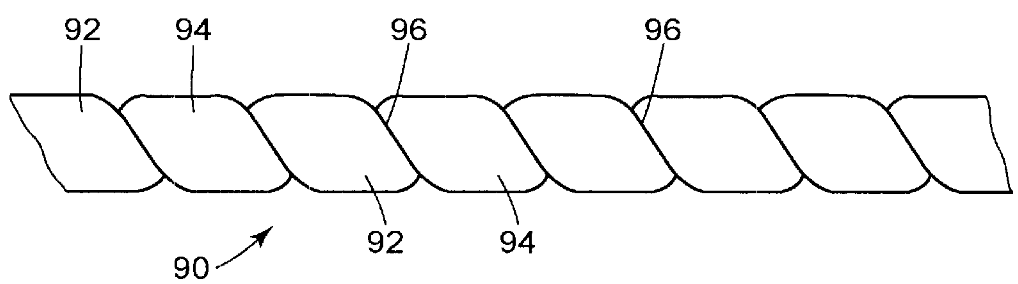
FIGS. 6A and 6B are schematic diagrams of a water-absorbing fiber having individual fibers of a first and a second water-absorbing resin twisted together to form a rope.

In another embodiment, the multicomponent SAP fiber comprises individual filaments of acidic resin and basic resin that are twisted together in the form of a rope. This embodiment is illustrated in FIGS. 6A and B, which illustrate a "twisted rope" embodiment of the present SAP fibers lengthwise and in cross section, respectively. In FIGS. 6A and B, a multicomponent SAP particle 90 comprises a filament 92 of acidic water-absorbing resin and a filament 94 of basic water-absorbing resin. In general, particle 90 can contain one or a plurality of filaments 92 or 94. Filaments 92 and 94 are in contact along zone of contact 96, thereby placing the acidic and basic resins in contact.

The "twisted rope" SAP fibers of FIGS. 6A and B also can be an embodiment wherein acidic resin filament 92 contains microdomains of a basic water-absorbing resin, i.e., is a multicomponent SAP fiber itself, and/or basic resin filament 94 contains microdomains of an acidic water-absorbing resin, i.e., also is a multicomponent SAP fiber itself. Filaments 92 and 94 then are intertwined to form multicomponent SAP fiber 90.

The embodiment of FIGS. 6A and B also can be a filament 92 and/or a filament 94 comprising a matrix resin having microdomains of acidic resin and/or basic resin. In this embodiment, filament 92 contains microdomains of an acidic resin, or microdomains of an acidic and a basic resin, and filament 94 contains microdomains of a basic resin, or microdomains of an acidic resin and a basic resin.

In another embodiment, the multicomponent SAP particles are agglomerated particles prepared from fine particles of an acidic water-absorbing resin and fine particles of a basic water-absorbing resin. Typically, a fine resin particle has a diameter of less than about 200 microns ($\mu$), such as about 0.01 to about 180$\mu$. The agglomerated multicomponent SAP particles are similar in structure to the particle depicted in FIG. 2. With respect to the agglomerated SAP particles, contact between the acidic resin and basic resin particles is sufficient such that the particles have sufficient dry agglomeration (i.e., in the dry state) and wet agglomeration (i.e., in the hydrogel state) to retain single particle properties, i.e., the particles do not disintegrate into their constituent fine particles of acidic resin and basic resin.

In particular, the agglomerated particles have sufficient dry agglomeration to withstand fracturing. The dry agglomerated particles typically have an elastic character and, therefore, are not friable. The agglomerated particles also have sufficient wet strength to exhibit a property termed "wet agglomeration." Wet agglomeration is defined as the ability of an agglomerated multicomponent SAP particle to retain its single particle nature upon hydration, i.e., a lack of deagglomeration upon hydration. Wet agglomeration is determined by positioning fifty agglomerated SAP particles on a watch glass and hydrating the particles with 20 times their weight of a 1% (by weight) sodium chloride solution (i.e., 1% saline). The particles are spaced sufficiently apart such that they do not contact one another after absorbing the saline and swelling. The SAP particles are allowed to absorb the saline solution for one hour, then the number of SAP particles is recounted under a microscope. The multicomponent SAP particles pass the wet agglomeration test if no more than about 53 hydrated particles are counted.

The multicomponent SAP particles of the present invention therefore comprise an acidic resin and a basic resin in a weight ratio of about 80:20 to about 60:40, and preferably about 75:25 to about 65:35. To achieve the full advantage of the present invention, the weight ratio of acidic resin to basic resin in a multicomponent SAP particle is about 70:30 to about 65:35. The acidic and basic resins can be distributed homogeneously or nonhomogeneously throughout the SAP particle.

The present multicomponent SAP particles contain at least about 50%, and preferably at least about 70%, by weight of acidic resin plus basic resin. To achieve the full advantage of the present invention, a multicomponent SAP particle contains about 80% to 100% by weight of the acidic resin plus basic resin. Components of the present SAP particles, other than the acidic and basic resin, typically, are matrix resins or other minor optional ingredients.

The multicomponent SAP particles of the present invention can be in any form, either regular or irregular, such as granules, fibers, beads, powders, flakes, or foams, or any other desired shape, such as a sheet of the multicomponent SAP. In embodiments wherein the multicomponent SAP is prepared using an extrusion step, the shape of the SAP is determined by the shape of the extrusion die. The shape of the multicomponent SAP particles also can be determined by other physical operations, such as milling or by the method of preparing the particles, such as agglomeration.

In one preferred embodiment, the present SAP particles are in the form of a granule or a bead, having a particle size of about 10 to about 10,000 microns ($\mu$m), and preferably about 100 to about 1,000 $\mu$m. To achieve the full advantage of the present invention, the multicomponent SAP particles have a particle size of about 150 to about 800 $\mu$m.

A "microdomain" is defined as a volume of an acidic resin or a basic resin that is present in a multicomponent SAP particle. Because each multicomponent SAP particle contains at least one microdomain of an acidic resin, and at least one microdomain of a basic resin, a microdomain has a volume that is less than the volume of the multicomponent SAP particle. A microdomain, therefore, can be as large as about 90% of the volume of multicomponent SAP particles.

Typically, a microdomain has a diameter of about 750 $\mu$m or less, and preferably about 100 $\mu$m or less. To achieve the full advantage of the present invention, a microdomain has a diameter of about 20 $\mu$m or less. The multicomponent SAP particles also contain microdomains that have submicron diameters, e.g., microdomain diameters of less than 1 $\mu$m, preferably less than 0.1 $\mu$m, to about 0.01 $\mu$m. A microdomain also can be the entire filament of a twisted rope form of a multicomponent SAP fiber.

In another preferred embodiment, the multicomponent SAP particles are in the shape of a fiber, i.e., an elongated, acicular SAP particle. The fiber can be in the shape of a cylinder, for example, having a minor dimension (i.e., diameter) and a major dimension (i.e., length). The fiber also can be in the form of a long filament that can be woven. Such filament-like fibers have a weight of below about 80 decitex, and preferably below about 70 decitex, per filament, for example, about 2 to about 60 decitex per filament. Tex is the weight in grams per one kilometer of fiber. One tex equals 10 decitex. For comparison, poly(acrylic acid) is about 0.78 decitex (0.078 tex), and poly(vinylamine) is about 6.1 decitex (0.61 decitex).

Cylindrical multicomponent SAP fibers have a minor dimension (i.e., diameter of the fiber) less than about 1 mm, usually less than about 500 $\mu$m, and preferably less than 250 $\mu$m, down to about 10 $\mu$m. The cylindrical SAP fibers can have a relatively short major dimension, for example, about 1 mm, e.g., in a fibrid, lamella, or flake-shaped article, but generally the fiber has a length of about 3 to about 100 mm. The filament-like fibers have a ratio of major dimension to minor dimension of at least 500 to 1, and preferably at least 1000 to 1, for example, up to and greater than 10,000 to 1.

Each multicomponent SAP particle contains one or more microdomains of an acidic water-absorbing resin and one or more microdomains of a basic water-absorbing resin. As illustrated hereafter, the microdomain structure of the present SAP particles provides improved fluid absorption (both in amount of fluid absorbed and retained, and rate of absorption) compared to an SAP comprising a simple mixture of discrete acidic SAP resin particles and discrete basic SAP resin particles. In accordance with another important feature of the present invention, the present multicomponent SAP particles also demonstrated improved permeability, both through an individual particle and between particles. The present SAP particles, therefore, have an improved ability to rapidly absorb a fluid, even in “gush” situations, for example, when used in diapers to absorb urine.

The features of good permeability, absorption and retention properties, especially of electrolyte-containing liquids, demonstrated by the present multicomponent SAP particles, is important with respect to practical uses of an SAP. These improved properties are attributed, in part, to the fact that electrolyte removal from the liquid is facilitated by contacting a single particle (which, in effect, performs an essentially simultaneous deionization of the liquid), as opposed to the liquid having to contact individual acidic and basic particles (which, in effect, performs a sequential two-step deionization).

If a blend of acidic resin particles and basic resin particles is used, the particles typically have a small particle size. A small particle size is required to obtain desirable desalination kinetics, because the electrolyte is removed in a stepwise manner, with the acidic resin removing the cation and the basic resin removing the anion. The electrolyte-containing fluid, therefore, must contact two particles for desalination, and this process is facilitated by small particle sized SAPs. Small particles, however, have the effect of reducing flow of the fluid through and between SAP particles, i.e., permeability is reduced and a longer time is required to absorb the fluid.

In addition, in practical use, such as in diapers, SAPs are used in conjunction with a cellulosic pulp. If a blend of acidic resin particles and basic resin particles is used as the SAP, the cellulosic pulp can cause a separation between the acidic resin particles and basic resin particles, which adversely affects desalination. The present multidomain composites overcome this problem because the acidic resin and basic resin are present in a single particle. The introduction of cellulosic pulp, therefore, cannot separate the acidic and basic resin and cannot adversely affect desalination by the SAP.

A single multicomponent SAP particle simultaneously desalinates an electrolyte-containing liquid. Desalination is essentially independent of particle size. Accordingly, the present multicomponent SAP particles can be of a larger size. These features allow for improved liquid permeability through and between the SAP particles, and results in a more rapid absorption of the electrolyte-containing liquid.

The following schematic reactions illustrate the reactions which occur to deionize, e.g., desalinate, an aqueous saline solution, and that are performed essentially simultaneously in a single microcomposite SAP particle, but are performed stepwise in a simple mixture of acidic and basic resins:

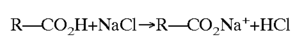

$$R{-}CO_2H + NaCl \rightarrow R{-}CO_2^-Na^+ + HCl$$

(acidic resin)

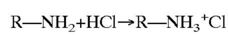

$$R{-}NH_2 + HCl \rightarrow R{-}NH_3^+Cl^-$$

(basic resin).

The present multicomponent SAP particles can be in a form wherein a microdomain of an acidic water-absorbing resin is in contact with a microdomain of a basic water-absorbing resin. In another embodiment, the SAP particles can be in a form wherein at least one microdomain of an acidic water-absorbing resin is dispersed in a continuous phase of a basic water-absorbing resin. Alternatively, the multicomponent SAP can be in a form wherein at least one microdomain of a basic resin is dispersed in a continuous phase of an acidic resin. In another embodiment, at least one microdomain of one or more acidic resin and at least one microdomain of one or more basic resin comprise the entire SAP particle, and neither type of resin is considered the dispersed or the continuous phase. In yet another embodiment, at least one microdomain of an acidic resin and at least one microdomain of a basic resin are dispersed in a matrix resin.

An acidic water-absorbing resin present in a multicomponent SAP particle can be either a strong or a weak acidic water-absorbing resin. The acidic water-absorbing resin can be a single resin, or a mixture of resins. The acidic resin can be a homopolymer or a copolymer. The identity of the acidic water-absorbing resin is not limited as long as the resin is capable of swelling and absorbing at least ten times its weight in water, when in a neutralized form. The acidic resin is present in its acidic form, i.e., about 75% to 100% of the acidic moieties are present in the free acid form. As illustrated hereafter, although the free acid form of a acidic water-absorbing resin is generally a poor water absorbent, the combination of an acidic resin and a basic resin in a present multicomponent SAP particle provides excellent water absorption and retention properties.

The acidic water-absorbing resin typically is a lightly crosslinked acrylic-type resin, such as lightly crosslinked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The other copolymerizable units can, for example, help improve the hydrophilicity of the polymer.

Ethylenically unsaturated carboxylic acid and carboxylic acid anhydride monomers useful in the acidic water-absorbing resin include, but are not limited to, acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, furmaric acid, tricarboxyethylene, and maleic anhydride.

Ethylenically unsaturated sulfonic acid monomers include, but are not limited to, aliphatic or aromatic vinyl sulfonic acids, such as vinylsulfonic acid, allyl sulfonic acid, vinyl toluene sulfonic acid, styrene sulfonic acid, acrylic and methacrylic sulfonic acids, such as sulfoethyl acrylate, sulfoethyl methacrylate, sulfopropyl acrylate, sulfopropyl methacrylate, 2-hydroxy-3-methacryloxypropyl sulfonic acid, and 2-acrylamide-2-methylpropane sulfonic acid.

As set forth above, polymerization of acidic monomers, and copolymerizable monomers, if present, most commonly is performed by free radical processes in the presence of a polyfunctional organic compound. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters, represented by the following formula (III), and bisacrylamides, represented by the following formula (IV), (III)

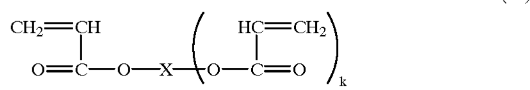

wherein x is ethylene, propylene, trimethylene, cyclohexyl, hexamethylene, 2-hydroxypropylene, —$(CH_2CH_2O)_nCH_2CH_2$—, or

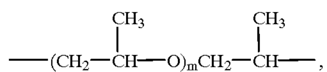

n and m are each an integer 5 to 40, and k is 1 or 2;

(IV)

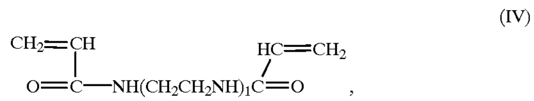

wherein l is 2 or 3.

The compounds of formula (III) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (IV) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used as crosslinkers. Especially preferred crosslinking agents are N,N'-methylenebisacrylamide, N,N'-methylenebismethacrylamide, ethylene glycol dimethacrylate, and trimethylolpropane triacrylate.

The acidic resin, either strongly acidic or weakly acidic, can be any resin that acts as an SAP in its neutralized form. The acidic resins typically contain a plurality of carboxylic acid, sulfonic acid, phosphonic acid, phosphoric acid, and/or sulfuric acid moieties. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, poly(aspartic acid), poly(lactic acid), and mixtures thereof. The preferred acidic resins are the polyacrylic acids.

The multicomponent SAPs can contain individual microdomains that: (a) contain a single acidic resin or (b) contain more than one, i.e., a mixture, of acidic resins. The multicomponent SAPs also can contain microdomains wherein, for the acidic component, a portion of the acidic microdomains comprise a first acidic resin or acidic resin mixture, and the remaining portion comprises a second acidic resin or acidic resin mixture.

Analogous to the acidic resin, the basic water-absorbing resin in the present SAP particles can be a strong or weak basic water-absorbing resins. The basic water-absorbing resin can be a single resin or a mixture of resins. The basic resin can be a homopolymer or a copolymer. The basic resin is capable of swelling and absorbing at least 10 times its weight in water, when in a charged form. The weak basic resin typically is present in its free base, or neutral, form, i.e., about 75% to about 100% of the basic moieties, e.g., amino groups, are present in a neutral, uncharged form. The strong basic resins typically are present in the hydroxide (OH) or bicarbonate ($HCO_3$) form.

The basic water-absorbing resin typically is a lightly crosslinked acrylic type resin, such as a poly(vinylamine). The basic water-absorbing resin can be any polymer containing a primary amine, a secondary amine, or a hydroxy functionality. The basic resin also can be a polymer, such as a lightly crosslinked polyethylenimine, a poly(allylamine), a poly(diallylamine), a copolymer of a dialkylamino acrylate and a monomer having primary amino, secondary amino, or hydroxy functionality, a guanidine-modified polystyrene, such as

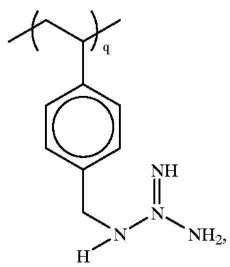

or a poly(vinylguanidine), i.e., poly(VG), a strong basic water-absorbing resin having the general structural formula (V)

(V)

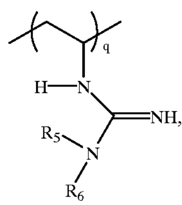

wherein q is a number from 10 to about 100,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic and aromatic groups. The lightly crosslinked basic water-absorbing resin can contain other copolymerizable units and is cross-linked using a polyfunctional organic compound, as set forth above with respect to the acidic water-absorbing resin.

A basic water-absorbing resin used in the present SAP particles typically contains an amino or a guanidino group. Accordingly, a water-soluble basic resin also can be crosslinked in solution by suspending or dissolving an uncrosslinked basic resin in an aqueous or alcoholic medium, then adding a di- or polyfunctional compound capable of cross-linking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $ZA(O_2)O—(CH_2)_n—OS(O)_2Z$, wherein n is 1 to 10, and Z is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate or methylene diisocyanate). Crosslinking agents also are disclosed in Pinschmidt, Jr. et al. U.S. Pat. No. 5,085,787, incorporated herein by reference, and in EP 450 923.

Conventionally, the crosslinking agent is water or alcohol soluble, and possesses sufficient reactivity with the basic resin such that crosslinking occurs in a controlled fashion, preferably at a temperature of about 25° C. to about 150° C. Preferred crosslinking agents are ethylene glycol diglycidyl ether (EGDGE), a water-soluble diglycidyl ether, and a dibromoalkane, an alcohol-soluble compound.

The basic resin, either strongly or weakly basic, therefore, can be any resin that acts as an SAP in its charged form. The basic resin typically contains amino or guanidino moieties. Examples of basic resins include a poly(vinylamine), a polyethylenimine, a poly(vinylguanidine), a poly (allylamine), or a poly(allylguanidine). Preferred basic resins include a poly(vinylamine), polyethylenimine, and poly (vinylguanadine). Analogous to microdomains of an acidic resin, the present multicomponent SAPs can contain microdomains of a single basic resin, microdomains containing a mixture of basic resins, or microdomains of different basic resins.

The present multicomponent SAPs can be prepared by various methods. It should be understood that the exact method of preparing a multicomponent SAP is not limited by the following embodiments. Any method that provides a particle having at least one microdomain of an acidic resin in contact with, or in close proximity to, at least one microdomain of a basic resin is suitable.

In one method, dry particles of a basic resin, optionally surface crosslinked, are admixed into a rubbery gel of an acidic resin. The resulting mixture is extruded, then dried, and annealed and optionally surface crosslinked to provide multicomponent SAP particles having microdomains of a basic resin dispersed in a continuous phase of an acidic resin. The drying and annealing steps can be separate steps, or can be performed simultaneously.

Alternatively, particles of an acidic resin, optionally surface crosslinked, can be admixed into a rubbery gel of a basic resin, and the resulting mixture is extruded and dried, and annealed and optionally surface crosslinked to provide multicomponent SAP particles having microdomains of an acidic resin dispersed in a continuous phase of a basic resin.

In another method, dry particles of an acidic resin can be admixed with dry particles of a basic resin, and the resulting mixture is formed into a hydrogel, then extruded, and annealed to form multicomponent SAP particles.

In yet another method, a rubbery gel of an acidic resin and a rubbery gel of a basic resin, each optionally surface crosslinked, are coextruded, and the coextruded product is dried, and annealed and optionally surface crosslinked, to form multicomponent SAP particles containing microdomains of the acidic resin and the basic resin dispersed throughout the particle.

Another method utilizes spinning technology, wherein a first polymer, e.g., poly(vinylamine), is spun in the form of a filament, then the freshly spun filament is coated with a second polymer, e.g., poly(acrylic acid), to form (after drying) a core-sheath multicomponent SAP fiber. The fiber then is annealed at an elevated temperature.

In yet another method, a filament of an acidic resin is prepared by standard spinning techniques, and a filament of a basic resin is prepared by standard spinning techniques.

Figure 6B:
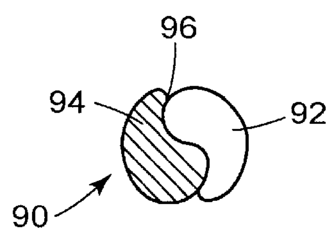

The two filaments then are twisted together, before and/or after optional surface crosslinking, and then dried and annealed to form multicomponent SAP fibers, as illustrated in FIG. 6.

The method of preparing the present multicomponent SAP particles, therefore, is not limited, and does not require an extrusion step. Persons skilled in the art are aware of other methods of preparation wherein the multicomponent SAP contains at least one microdomain of an acidic resin and at least one microdomain of a basic resin in contact with one another. One example is agglomeration of fine particles of at least one acidic resin and at least one basic resin with each other, and optionally a matrix resin, followed by an annealing step, to provide a multicomponent SAP particle containing microdomains of an acidic resin in contact with microdomains of a basic resin. The multicomponent SAP particles can be ground to a desired particle size, or can be prepared by techniques that yield the desired particle size. Other nonlimiting methods of preparing an SAP particle of the present invention are set forth in the examples.

In embodiments wherein an acidic resin and a basic resin are present as microdomains within a matrix of a matrix resin, particles of an acidic resin and a basic resin are admixed with a rubbery gel of a matrix resin, and the resulting mixture is extruded, then dried and annealed (as separate steps or simultaneously), to form multicomponent SAP particles having microdomains of an acidic resin and a basic resin dispersed in a continuous phase of a matrix resin. Alternatively, rubbery gels of an acidic resin, basic resin, and matrix resin can be coextruded, then annealed, to provide a multicomponent SAP containing microdomains of an acidic resin, a basic resin, and a matrix resin dispersed throughout the particle. In this embodiment, the acidic resin, basic resin, and resulting multicomponent SAP, each can be optionally surface crosslinked.

The matrix resin is any resin that allows fluid transport such that a liquid medium can contact the acidic and basic resin. The matrix resin typically is a hydrophilic resin capable of absorbing water. Nonlimiting examples of matrix resins include poly(vinyl alcohol), poly(N-vinylformamide), polyethylene oxide, poly(meth)acrylamide, poly (hydroxyethyl acrylate), hydroxyethylcellulose, methylcellulose, and mixtures thereof. The matrix resin also can be a conventional water-absorbing resin, for example, a polyacrylic acid neutralized greater than 25 mole %, and typically greater than 50 mole %.

In preferred embodiments, the acidic resin, the basic resin, and/or the multicomponent SAP particles are surface treated. Surface treatment results in surface crosslinking of the particle. In especially preferred embodiments, the acidic and/or basic resins comprising the multicomponent SAP particles are surface treated and/or annealed, and the entire multicomponent SAP particle is surface treated. It has been found that surface treating of an acidic resin, a basic resin, and/or a multicomponent SAP particle of the present invention enhances the ability of the resin or multicomponent SAP particle to absorb and retain aqueous media under a load.

Surface crosslinking is achieved by contacting an acidic resin, a basic resin, and/or a multicomponent SAP particle with a solution of a surface crosslinking agent to wet predominantly only the outer surfaces of the resin or SAP particle. Surface crosslinking and drying of the resin or multicomponent SAP particle then is performed, preferably by heating at least the wetted surfaces of the resin or multicomponent SAP particles.

Typically, the resins and/or SAP particles are surface treated with a solution of a surface crosslinking agent. The solution contains about 0.01% to about 4%, by weight, surface crosslinking agent, and preferably about 0.4% to about 2%, by weight, surface crosslinking agent in a suitable solvent, for example, water or an alcohol. The solution can be applied as a fine spray onto the surface of freely tumbling resin particles or multicomponent SAP particles at a ratio of about 1:0.01 to about 1:0.5 parts by weight resin or SAP particles to solution of surface crosslinking agent. The surface crosslinker is present in an amount of 0% to about 5%, by weight of the resin or SAP particle, and preferably 0% to about 0.5% by weight. To achieve the full advantage of the present invention, the surface crosslinker is present in an amount of about 0.001% to about 0.1% by weight.

The crosslinking reaction and drying of the surface-treated resin or multicomponent SAP particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the resin or multicomponent SAP particles, and any other method of drying the resin or multicomponent SAP particles, such as microwave energy, or the such as, can be used.

With respect to the basic resin, or multicomponent SAP particles having a basic resin present on the exterior surface of the particles, suitable surface crosslinking agents include di- or polyfunctional molecules capable of reacting with amino groups and crosslinking a basic resin. Preferably, the surface crosslinking agent is alcohol or water soluble and possesses sufficient reactivity with a basic resin such that crosslinking occurs in a controlled fashion at a temperature of about 25° C. to about 150° C.

Nonlimiting examples of suitable surface crosslinking agents for basic resins include:

(a) dihalides and disulfonate esters, for example, compounds of the formula $$Y-(CH_2)_p-Y,$$

wherein p is a number from 2 to 12, and Y, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, such as epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, such as oxalic acid, adipic acid, succinic acid, dodecanoic acid, malonic acid, and glutaric acid, and esters, anhydrides, and acid chlorides derived therefrom;

(g) organic titanates, such as TYZOR AA, available from E. I. DuPont de Nemours, Wilmington, Del.;

(h) melamine resins, such as the CYMEL resins available from Cytec Industries, Wayne, N.J.;

(i) hydroxymethyl ureas, such as N,N'-dihydroxymethyl-4,5-dihydroxyethylene urea;

(j) multifunctional isocyanates, such as toluene diisocyanate, isophorone diisocyanate, methylene diisocyanate, xylene diisocyanate, and hexamethylene diisocyanate;

(k) β-hydroxyalkylamides as disclosed in U.S. Pat. No. 4,076,917, incorporated herein by reference, such as PRIMID™ XL-552, available from EMS-CHEMIE AG, Dornat, Switzerland; and (l) other crosslinking agents for basic water-absorbing resins known to persons skilled in the art.

A preferred surface crosslinking agent is a dihaloalkane, ethylene glycol diglycidyl ether (EGDGE), PRIMID™ XL-552, or a mixture thereof, which crosslink a basic resin at a temperature of about 25° C. to about 150° C. Especially preferred surface crosslinking agents are dibromoalkanes containing 3 to 10 carbon atoms, EGDGE, and PRIMID™ XL-552.

With respect to the acidic water-absorbing resins, or multicomponent SAP particles having an acidic resin on the exterior surface of the particles, suitable surface crosslinking agents are capable of reacting with acid moieties and crosslinking the acidic resin. Preferably, the surface crosslinking agent is alcohol soluble or water soluble, and possesses sufficient reactivity with an acidic resin such that crosslinking occurs in a controlled fashion, preferably at a temperature of about 25° C. to about 150° C.

Nonlimiting examples of suitable surface crosslinking agents for acidic resins include:

(a) polyhydroxy compounds, such as glycols and glycerol;

(b) metal salts;

(c) quaternary ammonium compounds;

(d) a multifunctional epoxy compound;

(e) an alkylene carbonate, such as ethylene carbonate or propylene carbonate;

(f) a polyaziridine, such as 2,2-bishydroxymethyl butanol tris[3-(1-aziridine propionate]);

(g) a haloepoxy, such as epichlorhydrin;

(h) a polyamine, such as ethylenediamine;

(i) a polyisocyanate, such as 2,4-toluene diisocyanate;

(j) β-hydroxyalkylamides as disclosed in U.S. Pat. No. 4,076,917, incorporated herein by reference, such as PRIMID™ XL-552, available from EMS-CHEMIE AG, Dornat, Switzerland; and (k) other crosslinking agents for acidic water-absorbing resins known to persons skilled in the art.

In addition to, or in lieu of, surface treating, the entire SAP particle is annealed to improve water absorption and retention properties under a load. It has been found that heating a resin for a sufficient time at a sufficient temperature improves the absorption properties of the resin.

It has been shown that heating an SAP particle for about 20 to about 120 minutes at a temperature of about 60° C. to about 200° C. improves absorption properties. Preferably, annealing is performed for about 30 to about 100 minutes at about 80° C. to about 150° C. To achieve the full advantage of annealing, the SAP particles are annealed for about 40 to about 90 minutes at about 100° C. to about 140° C. The annealing step can be a separate heating step, or can be performed simultaneously with surface crosslinking of the SAP particle. In preferred embodiments, the multicomponent SAP particles are annealed at a temperature greater than the glass transition temperature, i.e., the Tg, of at least one of the water-absorbing resins present in the SAP particles, however, an In accordance with an important feature of the present invention, a strong acidic resin can be used with either a strong basic resin or a weak basic resin, or a mixture thereof. A weak acidic resin can be used with a strong basic resin or a weak basic resin, or a mixture thereof. Preferably, the acidic resin is a weak acidic resin and the basic resin is a weak basic resin. This result is unexpected in view of the ion exchange art wherein a combination of a weak acidic resin and a weak basic resin does not perform as well as other combinations, e.g., a strong acidic resin and a strong basic resin. In more preferred embodiments, the weak acidic resin, the weak basic resin, and/or the multicomponent SAP particles are surface crosslinked and annealed.

As previously discussed, sodium poly(acrylate) conventionally is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

However, an acidic resin in the free acid form, or a basic resin in the free base form, typically do not function as a commercially useful SAP because there is no ionic charge on either type of polymer. A poly(acrylic acid) resin, or a poly(vinylamine) resin, are neutral polymers, and, accordingly, do not possess the polyelectrolytic properties necessary to provide SAPs useful commercially in diapers, catamenial devices, and similar absorbent articles. The driving force for water absorption and retention, therefore, is lacking. This is illustrated in Tables 2–4 showing the relatively poor absorption and retention properties for a neutral poly(DAEA) and other basic and acidic resins in absorbing synthetic urine. However, when converted to a salt, an acidic resin, such as a polyacrylic acid, or a basic resin, such as a poly(dialkylaminoalkyl (meth)acrylamide), then behave as a commercially useful SAP.

It has been found that basic resins, in their free base form, are useful components in superabsorbent materials further containing an acidic water-absorbing resin. For example, a superabsorbent material comprising an admixture of a poly (dialkylaminoalkyl (meth)acrylamide) and an acidic water-absorbing resin, such as polyacrylic acid, demonstrates good water absorption and retention properties. Such an SAP material comprises two uncharged, slightly crosslinked polymers, each of which is capable of swelling and absorbing aqueous media. When contacted with water or an aqueous electrolyte-containing medium, the two uncharged polymers neutralize each other to form a superabsorbent material. This also reduces the electrolyte content of the medium absorbed by polymer, further enhancing the polyelectrolyte effect. Neither polymer in its uncharged form behaves as an SAP by itself when contacted with water. However, superabsorbent materials, which contain a simple mixture of two resins, one acidic and one basic, are capable of acting as an absorbent material because the two resins are converted to their polyelectrolyte form. These superabsorbent materials have demonstrated good water absorption and retention properties. However, the present multicomponent SAP particles, containing at least one microdomain of an acidic resin and at least one microdomain of a basic resin, exhibit improved water absorption and retention, and improved permeability, over simple mixtures of acidic resin particles and basic resin particles.

In the present multicomponent SAP particles, the weak basic resin is present in its free base, e.g., amine, form, and the acidic resin is present in its free acid form. It is envisioned that a low percentage, i.e., about 25% or less, of the amine and/or acid functionalities can be in their charged form. The low percentage of charged functionalities does not adversely affect performance of the SAP particles, and can assist in the initial absorption of a liquid. A strong basic resin is present in the hydroxide or bicarbonate, i.e., charged, form.

The present multicomponent SAP particles are useful in articles designed to absorb large amounts of liquids, especially electrolyte-containing liquids, such as in diapers and catamenial devices.

The following nonlimiting examples illustrate the preparation of multicomponent SAP particles of the present invention.

In the test results set forth below, the multicomponent SAP particles of the present invention were tested for absorption under no load (AUNL) and absorption under load at 0.28 psi and 0.7 psi (AUL (0.28 psi) and AUL (0.7 psi)). Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g +/−0.001 g) is carefully scattered onto a 140-micron, water-permeable mesh attached to the base of a hollow Plexiglas cylinder with an internal diameter of 25 mm. The sample is covered with a 100 g cover plate and the cylinder assembly weighed. This gives an applied pressure of 20 g/cm$^2$ (0.28 psi). Alternatively, the sample can be covered with a 250 g cover plate to give an applied pressure of 51 g/cm$^2$ (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact.

EXAMPLE 1

Preparation of Poly(acrylic acid) 0% Neutralized (Poly(AA) DN=0)

A monomer mixture containing acrylic acid (270 grams), deionized water (810 grams), methylenebisacrylamide (0.4 grams), sodium persulfate (0.547 grams), and 2-hydroxy-2-methyl-1-phenyl-propan-1-one (0.157 grams) was prepared, then sparged with nitrogen for 15 minutes. The monomer mixture was placed into a shallow glass dish, then the monomer mixture was polymerized at an initiation temperature of 10° C. under 20 mW/cm$^2$ of UV light for about 12 to about 15 minutes. The resulting poly(AA) was a rubbery gel.

The rubbery poly(AA) gel was cut into small pieces, then extruded three times through a KitchenAid Model K5SS mixer with meat grinder attachment. During extrusion, sodium metabisulfite was added to gel to react with unreacted monomer. The extruded gel was dried in a forced-air oven at 145° C. for 90 minutes, and finally ground and sized through sieves to obtain the desired particle size of about 180 to about 710 $\mu$m (microns).

This procedure provided a lightly cross-linked polyacrylic acid with a degree of neutralization of zero (DN=0). The polyacrylic acid (DN=0) absorbed 119.5 g of 0.1 M sodium hydroxide (NaOH) per gram of polymer and 9.03 g synthetic urine per gram of polymer under a load of 0.7 psi.

EXAMPLE 2

Preparation of Poly(dimethylaminoethyl acrylamide) (Poly (DAEA))

A monomer mixture containing 125 grams N-(2-dimethylaminoethyl) acrylamide (DAEA), 300 grams deionized water, 0.6 gram methylenebisacrylamide, and 0.11 grams V-50 initiator (i.e., 2,2'-azobis(2-amidinopropane) hydrochloride initiator available from Wako Pure Chemical Industries, Inc., Osaka, Japan) was sparged with argon for 15 minutes. Then the resulting reaction mixture was placed in a shallow dish and polymerized under 15 mW/cm$^2$ of UV light for 25 minutes. The polymerization was exothermic, eventually reaching about 100° C. The resulting lightly crosslinked poly(DAEA) was a rubbery gel. The rubbery poly(DAEA) gel was crumbled by hand, then dried at 60° C. for 16 hours, and finally ground and sized through sieves to obtain the desired particle size.

EXAMPLE 3

Preparation of Poly(dimethylaminopropyl methacrylamide) (Poly(DMAPMA))

A monomer mixture containing DMAPMA monomer (100 grams), deionized water (150 grams), methylenebisacrylamide (0.76 grams) and V-50 initiator (0.72 grams) was placed in a glass beaker. The monomer mixture was purged with argon for 25 minutes, covered, and then placed in an oven at about 60° C. for about 60 hours. The resulting lightly crosslinked poly(DMAPMA) was a rubbery gel. The rubbery poly(DMAPMA) gel was crumbled by hand, dried at 60° C. for 16 hours, and then ground and sized through sieves to obtain the desired particle size.

EXAMPLE 4

Preparation of a Poly(N-vinylformamide) and a Poly(vinylamine) (PolyVAm)

A monomer mixture containing N-vinylformamide (250 grams), deionized water (250 grams), methylenebisacrylamide (1.09) grams), and V-50 initiator (0.42 grams) was placed in a shallow dish, then polymerized under an ultraviolet lamp as set forth in Example 1 until the mixture polymerized into a rubbery gel. The lightly crosslinked poly(N-vinylformamide) then was hydrolyzed with a sodium hydroxide solution to yield a lightly crosslinked poly(vinylamine), i.e., poly(VAm).

EXAMPLE 5

Preparation of a Strong Acidic Water-Absorbing Resin

A monomer mixture containing acrylic acid (51 grams), 2-acrylamido-2-methyl-1-propanesulfonic acid (AMPS, 25.8 grams), deionized water (230 grams), methylenebisacrylamide (0.088 grams), sodium persulfate (0.12 grams), and 2-hydroxy-2-methyl-1-phenylpropan-1-one (0.034 grams) was prepared, then placed in shallow dish and polymerized under an ultraviolet lamp as set forth in Example 1 until the monomer mixture polymerizes into rubbery gel.

The gel was cut into small pieces then extruded through a KitchenAid Model K5SS mixer with a meat grinder attachment. The extruded gel then was dried in a forced-air oven at 120° C., ground, and sized through sieves to obtain the desired particle size.

The resulting lightly crosslinked acidic resin contained 15 mole percent strong acid functionality (—$SO_3H$) and 85 mole percent weak acid functionality (—$CO_2H$).

EXAMPLE 6

Preparation of a Crosslinked Poly(vinyl alcohol-co-vinylamine) Resin

Poly(vinyl alcohol-co-vinylamine) (50 grams, 6 mol % vinylamine), available from Air Products Inc., Allentown, Pa., was dissolved in 450 grams of deionized water in a glass jar to form a viscous solution. Ethylene glycol diglycidyl ether (0.2 grams) was added to the viscous solution, with stirring. The jar then was covered and placed in a 60° C. oven for 16 hours to yield a rubbery gel of a lightly crosslinked poly(vinyl alcohol-co-vinylamine).

EXAMPLE 7

Preparation of a Crosslinked Poly(vinylamine) Resin

To 100 g of an 8% by weight aqueous poly(vinylamine) solution was added about 2 mol % (0.66 g) of ethylene glycol diglycidyl ether (EGDGE). The resulting mixture was stirred for about 5 minutes to dissolve the EGDGE, then the homogeneous mixture was placed in an oven, heated to about 60° C., and held for two hours to gel. The resulting gel then was extruded three times, and dried to a constant weight at 60° C. The dried, lightly crosslinked poly(vinylamine) (poly(VAm)) then was cryogenically milled to form a granular material (about 180 to about 710 μm). The crosslinked poly(VAm) absorbed 59.12 g/g of 0.1 M hydrochloric acid under no load, and 17.3 g/g of synthetic urine under a load of 0.7 psi.

EXAMPLE 8

Preparation of Poly(vinylquanadine) (Poly(VG))

To 500 ml of an aqueous solution of poly(vinylamine) (1.98% solids, 93% hydrolyzed) was added 38.5 ml of 6M hydrochloric acid and 9.65 g of cyanamide ($H_2NCN$). The resulting solution was heated under reflux for 8 hours. The solution next was diluted to a volume of 3L (liters) with a 5% sodium hydroxide solution, then ultrafiltered ($M_w$ cut off of 100,000) with 15L of a 5% sodium hydroxide solution, followed by 15L of deionized water. The resulting product was concentrated to a 2.6% solids solution, having a pH 11.54. A poly(vinylamine) solution has a pH 10.0. The 2.6% solids solution gave a negative silver nitrate test, and a gravimetric analysis of the polymer, after the addition of HCl, gave the following composition: vinylguanidine 90%, vinylformamide 7%, and vinylamine 3%. Infrared analysis shows a strong absorption at 1651 $cm^1$, which is not present in poly(vinylamine), and corresponds to a C═N stretch.

EXAMPLE 9

Preparation of a Crosslinked Poly(VG) Resin

The 2.6% solids solution of Example 8 was further concentrated to 12.5% solids by distillation. To this 12.5% solids solution was added 1 mole % EGDGE, and the resulting solution then was heated in a 60° C. oven for 5 hours to form a gel of lightly crosslinked poly (vinylguanidine).

EXAMPLE 10

Preparation of Poly(acrylic acid) Fibers by Dry Spinning

A spinning solution was prepared by concentrating an aqueous 35% (w/w) solution of uncrosslinked poly(acrylic acid) (poly(AA)), molecular weight about 250,000, to 55% (w/w). To this solution was added EGDGE (0.5% to 5% mol/mol poly(AA)) and triethylamine (5% mol/mol poly (AA)), and the resulting mixture was mixed to produce a homogeneous spinning solution. The viscosity of the spinning solution, at 55% (w/w), was 13,000 cps (by Reverse Flow Viscometer, size 8, at 25° C.). The spinning solution was placed in a Petri dish and fibers were drawn vertically upwards to a rotating drum (diameter of 15.5 cm). The pull off speed was about 54 rpm with a filament draw length of 500 mm. The drawn fibers were cured either by microwave using 720 watts (W) power (2 minutes for 5% EGDGE) or by a conventional fan-assisted oven at 60° C. (60 minutes for 5% EGDGE). The time needed to cure the fiber was dependent upon the concentration of EGDGE. In the preparation of poly(AA) by dry spinning, the concentration of EGDGE in the spinning solution typically is about 0.5 to about 5% (mol/mol poly(AA)). The addition of triethylamine as a cure catalyst resulted in a faster cure, which occurred at a lower temperature.

The resulting poly(AA) fibers were about 25 μm in diameter and 0.71 denier (0.078 tex). The fibers absorbed about 69.9 g/g of 0.1 M NaOH at no load after 1 hour, and about 17.6 g/g of synthetic urine at 0.28 psi after 1 hour.

EXAMPLE 11

Preparation of Poly(vinylamine) Fibers by Wet Spinning

A spinning solution was prepared by concentrating a 6% w/w aqueous solution of poly(VAm) to 10% w/w poly (VAm) (molecular weight about 190,000). EGDGE (0.025 mol %) was added to the poly(VAm) solution, and mixed to provide a homogeneous solution. The solution then was heated for about 30 minutes at about 40° C., and was spinnable. The resulting spinning solution was introduced directly into a coagulation bath through a spinnerette submersed in a coagulating medium. The coagulation medium in the coagulation bath contained a mixture of EGDGE, typically 0.5% (w/w), and acetone. The concentration of EGDGE typically is about 0.5 to about 5% (w/w). The spinning solution was placed in a syringe fitted with a 23 gauge needle. The poly(VAm) was injected into the coagulating medium at a flow rate of 0.02 ml/min, and the resulting poly(VAm) was drawn off at a windup rate of 64 rpm. The diameter of the drum was 12 cm. The poly(VAm) fibers had a diameter of 28 μm and were 5.5 denier (0.61 tex). Curing was performed in an oven at 80° C. for 30 minutes. The poly(VAm) fiber absorbed 68.3 g/g (after 1 hour) and 73.5 g/g (after 3 hours) of 0.1 M hydrochloric acid under no load, and 19.6 g/g (after 1 hour) under a load of 0.28 psi.

Poly(VAm) fibers also were produced from the identical spinning solution using a dry-jet wet spinning technique. In this technique, the spinnerette was positioned above the coagulation bath and the fiber originally was spun in air, then pulled through the coagulation bath.

The physical properties of poly(AA) permit dry spinning of the polymer. Poly(AA) has a high extensional viscosity that allows stringing of the polymer solution and drawing of filaments, or fibers, from a poly(AA) spinning solution. Poly(VAm) does not have the physical properties necessary for dry spinning, and therefore is subjected to a wet spinning process. In the spinning of an acidic or a basic water-absorbing polymer, persons skilled in the art can determine whether a dry spinning or a wet spinning process should be used based on the properties of the resin.

EXAMPLE 12

Preparation of Twisted Rope Multicomponent SAP Fibers

A multicomponent SAP fiber of the present invention was prepared by twisting together a poly(AA) fiber of Example 10 and a poly(VAm) fiber of Example 11 to provide intimate contact between the acidic and basic water-absorbing resins. After twisting the acidic and basic water-absorbing fibers together, the resulting twisted rope fiber was annealed in a 125° C. oven for about 20 minutes. Twisted rope fibers containing a 1:1 mole ratio of poly(AA) of Example 10 and poly(VAm) of Example 11 absorbed aqueous media as follows:

| Aqueous Testing Medium | AUL[1)] (g/g) (after 1 hr) | | AUL[1)] (g/g) (after 4 hr) | |
|---|---|---|---|---|
| Synthetic urine | 33.0[4)] | (20.2)[3)] | 35.7 | (26.2) |
| | 30.4 | | 36.4 | |
| 0.9% saline | 24.1 | (19.6) | 25.4 | (21.3) |
| | 23.9 | | 24.6 | |
| Synthetic blood[2)] | 29.2 | (24.1) | 30.0 | (26.1) |
| | 27.2 | | 28.8 | |

[1)]Absorbance under load of 0.7 psi;
[2)]PLASMION ®, available from Rhone-Poulenc Rorer Bellon, Neilly sur Seine, Belgium;
[3)]the value in parentheses is the amount of aqueous medium absorbed by a commercial SAP fiber, i.e., OASIS ™, available from Allied Colloids, England, and is included for comparative purposes; and
[4)]absorption tests were run in duplicate.

In Example 12, the twisted rope was annealed after the fibers were twisted together. However, annealing of the individual fibers, prior to braiding, can be performed, in addition to annealing of the twisted rope fiber.

Although Example 12 is directed to a single fiber of a poly(AA) and a single fiber of a poly(VAm) twisted together in the form of a braid, a twisted rope fiber of the present invention also encompasses embodiments wherein one or more poly(AA) fibers and one or more poly(VAm) fibers are twisted together in the form of a braid. Accordingly, embodiments wherein one or a plurality of (e.g., 1 to 500) poly(AA) fibers twisted together with one or a plurality of (e.g., 1 to 500) poly(VAm) fibers also are within the scope of the present invention.

In the twisted fiber embodiment, the mole ratio of basic resin to acidic resin is about 0.5:1 to about 1:1, and preferably about 0.6:1 to about 0.8:1. To achieve the full advantage of the present invention, the mole ratio is about 0.65:1 to about 0.75:1.

The effect of cure time and cure temperature on absorbency of a 1:1 mole ratio twisted fiber of Example 12 was examined. The results of this test are summarized in Table 1.

TABLE 1

Effect of cure time and temperature on the absorbency of twisted fibers

| Time of cure (mins) | Temp of cure (° C.) | AUL[1)] (g/g) (after 1 hr) | AUL[1)] (g/g) (after 3 hr) |
|---|---|---|---|
| 30 | 80 | 33.08 | 37.66 |
| 10 | 125 | 38.41 | 40.03 |
| 20 | 125 | 55.46 | 63.21 |
| 30 | 125 | 33.53 | 36.80 |
| 120 | 125 | 29.28 | 32.11 |

[1)]amount of synthetic urine absorbed under a load of 0.7 psi.

The rate of absorption for the 1:1 mole ratio twisted fibers of Example 12, cured at 125° C. for 20 minutes, was compared to OASIS™ fibers, poly(VAm) fibers of Example 11, and poly(AA) fibers of Example 10. The results show that the annealed twisted SAP fibers absorb more rapidly than poly(VAm) and poly(AA) fibers, and over time outperforms OASIS™ fibers.

The following tables contain absorption and retention data for the multicomponent SAP particles of the present invention, for individual polymers present in the multicomponent SAP particles, and for simple admixtures of the dry resins present in the multicomponent SAP particles. The data shows a significant improvement in water absorption and retention for the present multicomponent SAP particles containing microdomains of an acidic and/or basic resin polymers within each particle compared to the individual resins and a simple admixture of the individual resins. The data in Tables 2–5 show the improved ability of multicomponent SAP particles of the present invention to absorb and retain an aqueous 0.9% saline solution.

TABLE 2

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(DAEA) alone[1)] | 9.6 | 8.1 | 23.9 | 13.5 | 9.3 | 24.2 |
| Polyacrylic Acid alone[2)] | 11.9 | 10.8 | 14.3 | 12.0 | 10.8 | 14.3 |
| SAP-1[3)] | 11.0 | 10.9 | 45.2 | 14.8 | 14.4 | 48.0 |
| SAP-2[4)] | 12.5 | 9.6 | 26.7 | 18.9 | 13.1 | 30.1 |
| SAP-3[5)] | 12.4 | 11.3 | 37.3 | 16.5 | 14.7 | 42.3 |
| SAP-4[6)] | 20.1 | 17.2 | 28.6 | 24.7 | 20.7 | 34.1 |
| SAP-5[7)] | 25.3 | 18.2 | 35.3 | 28.1 | 23 | 38 7 |

[1)]particle size--180–710 μm;
[2)]0% neutralization, particle size--180–710 μm, surface crosslinked--600 ppm EGDGE;
[3)]mixture of 60% poly(DAEA), particle sizes less than 180 nm, and 40% polyacrylic acid--0% neutralized;
[4)]mixture of 60% poly(DAEA), particle sizes less than 180 nm, and 40% polyacrylic acid--0% neutralized, crosslinked with 600 ppm EGDGE;
[5)]mixture of 60% poly(DAEA), particle size--180–710 μm, and 40% polyacrylic acid--0% neutralized;
[6)]mixture of 60% poly(DAEA), particle size--180–710 μm, and 40% polyacrylic acid--0% neutralized, crosslinked with 600 ppm EGDGE; and
[7)]mixture of 60% poly(DAEA), particle sizes less than 180 μm, and 40% polyacrylic acid--20% neutralized, particle size 180–710 μm.

TABLE 3

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(DMAPMA)[1)] | 10.2 | 8.6 | 18 | 11.4 | 10 | 18.3 |
| Poly(DMAPMA)[2)] | 9.3 | 5.2 | 17.4 | 11 | 6.9 | 17.8 |
| Polyacrylic acid[3)] | 11.9 | 10.8 | 14.3 | 12.0 | 10.8 | 14.3 |
| SAP-6[4)] | 14.5 | 10.9 | 18.8 | 17.2 | 14.3 | 20.9 |
| SAP-7[5)] | 14 | 12 | 38.7 | 17.9 | 15.7 | 43.6 |
| SAP-8[6)] | 12.5 | 10.4 | 24.8 | 14.5 | 12.4 | 24.8 |

[1)]Poly(DMAPMA), particle size less than 106 μm;
[2)]Poly(DMAPMA), particle size 106–180 μm;
[3)]Polyacrylic acid, particle size 180–710 μm--0% neutralized, surface crosslinked with 600 ppm EGDGE;
[4)]mixture of 60% Poly(DMAPMA), particle size 106–180 μm, and 40% polyacrylic acid--0% neutralized;
[5)]mixture of 60% Poly(DMAPMA), particle size <106 μm, and 40% polyacrylic acid--0% neutralized; and
[6)]mixture of 50% Poly(DMAPMA), and 50% polyacrylic acid--0% neutralized.

TABLE 4

| SAP | AUL (0.28 psi, 1 hr.) | AUL (0.7 psi, (1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(vinylamine) alone | 14.2 | 14.4 | 21.4 | 15 | 14.3 | 23.4 |
| SAP-9[1)] | 21.2 | 18.6 | 28.3 | 23.8 | 20.5 | 36.3 |
| Multicomponent SAP-6[2)] | | | | | | |
| 0[3)] | 14.9 | 12.8 | 53.8 | 16.9 | 15.6 | 55.4 |
| 100 | 37.5 | 30.1 | 45.5 | 37.5 | 30.1 | 45.5 |
| 200 | 36.2 | 30.4 | 48.5 | 35.9 | 30.2 | 47.4 |
| 400 | 34.6 | 30.6 | 44.9 | 34.6 | 30.6 | 46.2 |

[1)]mixture of 37% poly(vinylamine) and 63% poly(AA);
[2)]multicomponent SAP containing microdomains of poly(vinylamine) (<180 μm) as dispersed phase in poly(AA) (DN = 0) continuous phase, poly(vinylamine)/poly(AA) weight ratio--37/63; and
[3)]ppm surface crosslinking with EGDGE.

TABLE 5

| | | Coextruded Multicomponent SAP of Example 16 (37.4/62.6 weight ratio PEI/poly(AA)) | | | | | |
|---|---|---|---|---|---|---|---|
| PEI Gel (% Solids) | Cross-linker Level[1)] | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
| 20 | 1.0 | 23 | 19.5 | 32 | 24.3 | 20.8 | 34.9 |
| 10 | 1.5 | 20.1 | 16.2 | 28.4 | 22.4 | 18.1 | 31.9 |

[1)]mole % EGDGE.

Figure 7:
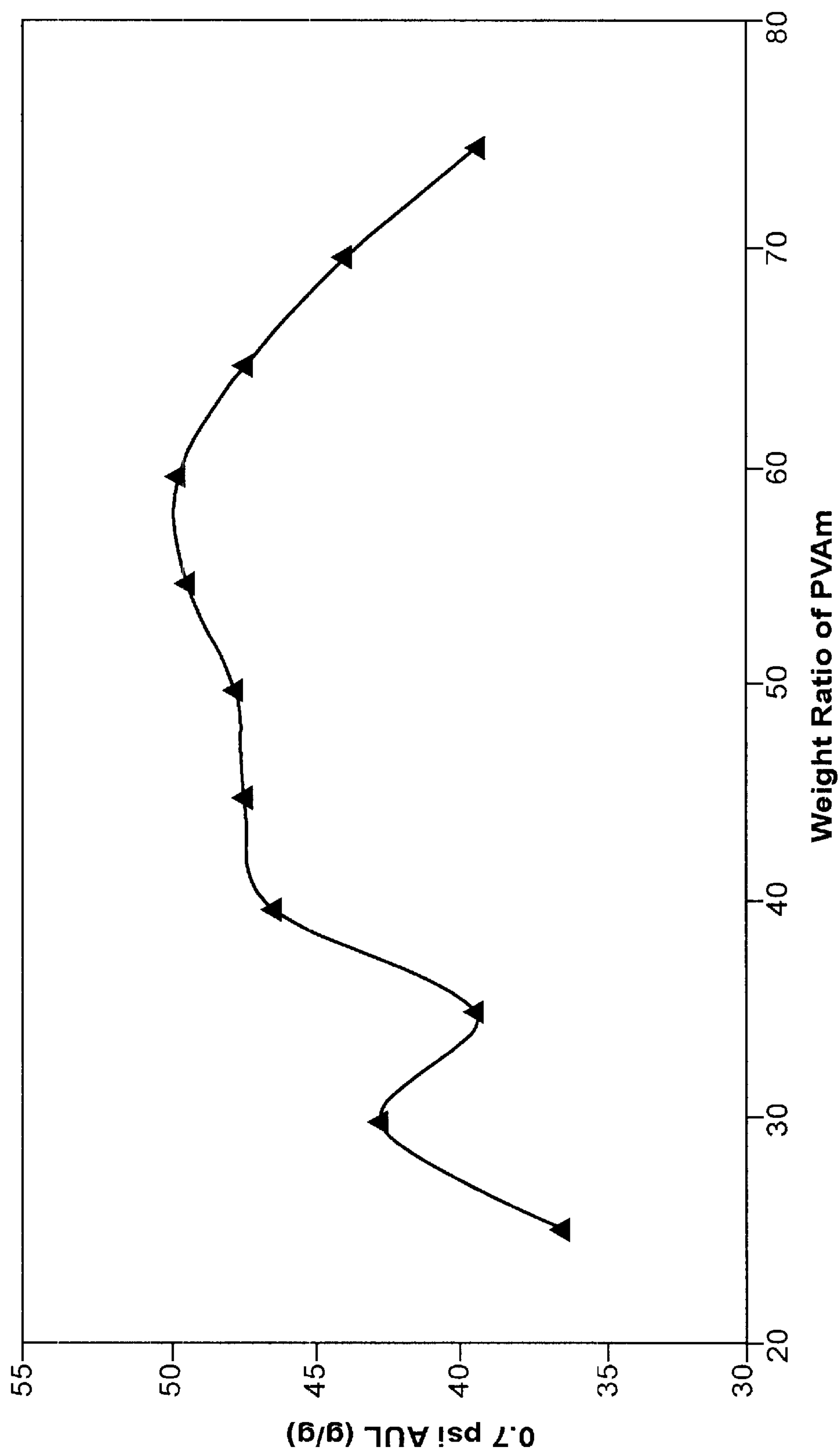
FIG. 7 contains a plot of AUL (g/g) at 0.7 psi (3 hours) for synthetic urine vs. weight ratio of poly(vinylamine) in the multicomponent superabsorbent particles.
Figure 8:
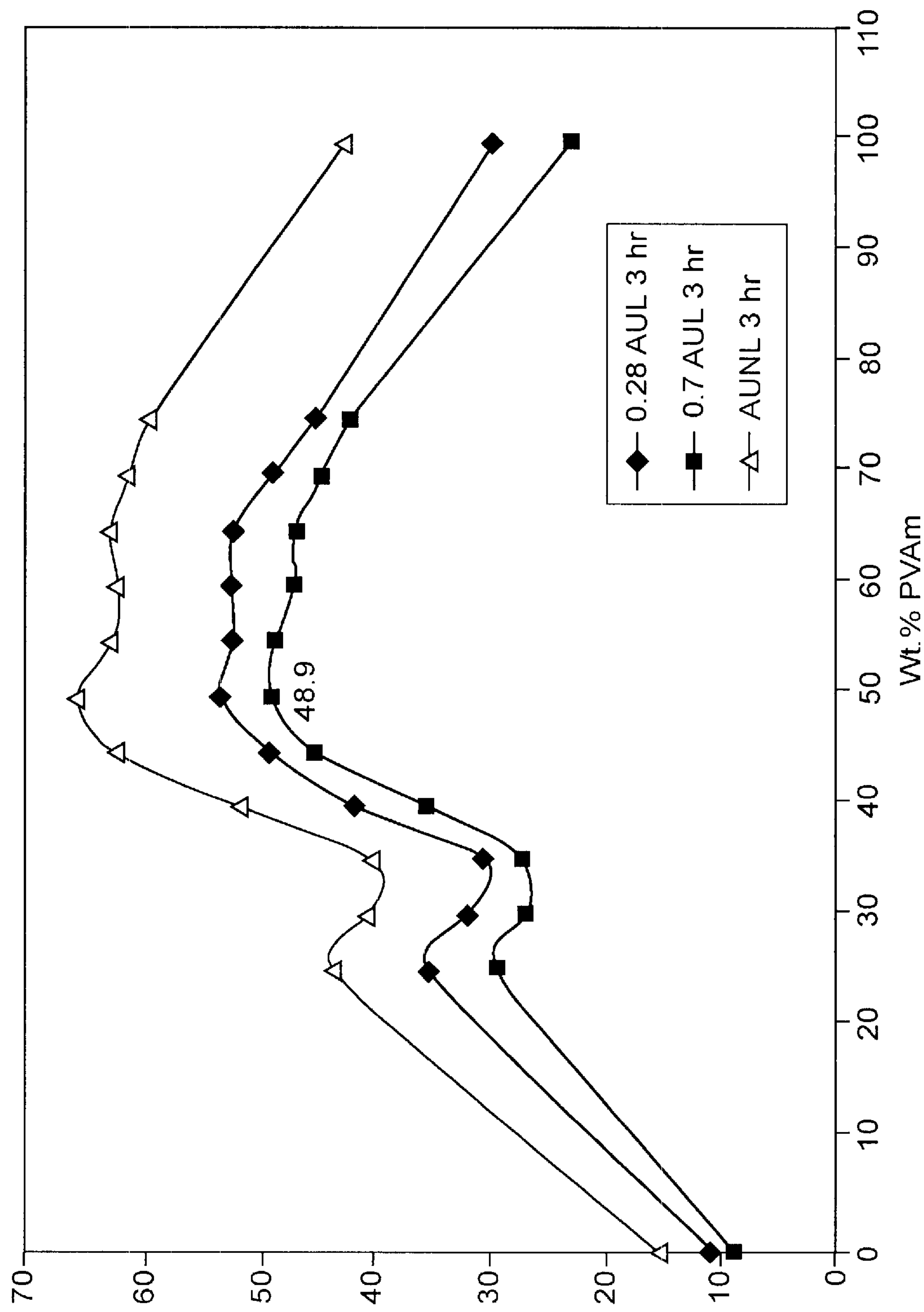
FIG. 8 contains plots of AUL (g/g) at 0.28 psi and 0.7 psi (3 hours), and of AUNL (3 hours), for synthetic urine vs. weight percent of poly(vinylamine) in the multicomponent superabsorbent particles.

The following examples further illustrate the unexpected and surprising results achieved by the multicomponent superabsorbent particles of the present invention. As illustrated in FIGS. 7 and 8, which are discussed in detail hereafter, a maximum AUL (0.7 psi) is achieved using multicomponent superabsorbent particles containing about 55 wt % poly(vinylamine) and about 45 wt % poly(acrylic acid), i.e., 55 g of synthetic urine per gram of particles, and an SFC (Saline Flow Conductivity) of greater than 300. Surprisingly, multicomponent superabsorbent particle containing 33 wt % poly(VAm) and 67 wt % poly(AA) demonstrated an AUL (0.7 psi) of 52 g/g and an SFC of greater than 300. FIGS. 7 and 8 show that multicomponent superabsorbent particles containing about 20 to about 40 wt % of poly(VAm) exhibit unexpectedly high absorption properties, and are substantially more economical than multicomponent superabsorbent particles containing a higher weight percent of poly(VAm).

In particular, FIGS. 7 and 8 show that multicomponent supersabsorbent particles exhibit a maximum polyelectrolytic effect when the particles contain about 50 to about 60 wt % polyvinylamine (polyVAm) and about 40 to about 50 wt % poly(AA). However, multicomponent superabsorbent particles exhibit a second AUL (0.7 psi) maximum between about 20 wt % and about 40 wt %, and particularly between about 25 wt % and about 35 wt % poly(VAm) (about 75 to about 65 wt % poly(AA)). This second AUL (0.7 psi) maxima corresponds to multicomponent superabsorbent particles optimized for the strongest polyelectrolytic effect attributed to poly(vinylamine).

With respect to FIG. 7, the multicomponent SAP particles used in the test were prepared as follows. A poly(VAm) solution was mixed with 4 mole % ethylene glycol diglycidyl ether (EGDGE) and placed in a 60° C. oven for 2 hours to form a firm gel. Separately, a poly(AA) gel (DN=0) was prepared using 0.07 mole % MBA as a crosslinker. The two gels were coextruded at the various concentrations necessary to provide the blend ratios illustrated in FIG. 7. The resulting gel blends were dried overnight at 60° C., and then milled and sized to 180–710 μm. The granules were coated with 50 ppm additional EGDGE in an 80/20 propylene glycol/water solution and then cured at 125° C. for 1 hour to provide surface crosslinking.

With respect to FIG. 8, the multicomponent SAP particles used in the test were prepared as follows. A poly(VAm) solution was cured as above with 2 mole % EGDGE. Separately, the PAA (DN=0) was prepared using 0.2 mole % MBA as a crosslinker. The two gels were coextruded at the various concentrations required to provide the blend ratios illustrated in FIG. 8. The resulting gel blends were dried and cured at 125° C. for 2 hours. The dry polymer then was milled and sized to 180–710 μm. No surface crosslinking was used. Samples in Tables 6–8 were prepared in the same manner as the samples in FIG. 8. The poly(allylamine) examples were dried overnight at 60° C., and then cured at 125° C. for 1 hour.

The following Tables 6 and 7 illustrate the superior absorption properties demonstrated by multicomponent superabsorbent particles containing a relatively low weight % of a basic resin. The multicomponent superabsorbent particles used in the tests summarized in Table 7 contained 30 weight percent of poly(vinylamine) and 70 weight percent polyacrylic acid (DN=0).

TABLE 6

| Wt %[1] Poly(VAm)[2] | Mole % EGDGE[3] in Poly(VAm) | Mole % MBA[4] in Poly(AA) | SFC | AUNL (g/g) | 3 hour AUL (g/) 0.28 psi | 3 hour AUL (g/) 0.7 psi |
|---|---|---|---|---|---|---|
| 28 | 1.5 | 0.35 | — | 60.8 | 50.2 | 46.5 |
| 30 | 1.5 | 0.2 | — | 64.7 | 54.5 | 48.1 |
| 33 | 1.0 | 0.35 | 454 | 64.1 | 53.6 | 52.0 |

[1]wt % poly(vinylamine) in multicomponent superabsorbent particles further containing poly(acrylic acid);
[2]poly(vinylamine) of 250,000 Daltons;
[3]amount of surface crosslinker (ethylene glycol diglycidyl ether) applied to the poly(vinylamine); and
[4]amount of surface crosslinker (methylenebis(acrylamide)) applied to the poly(acrylic acid).

TABLE 7

| Poly(VAm) (Daltons) | Mole % EGDGE[1] in Poly(VAm) | Mole % MBA[2] in Poly(AA) | SFC[3] | 4 Hour AUL (g/g) (0.7 psi load) |
|---|---|---|---|---|
| 60,000 | 1.5 | 0.2 | 1546 | 53 |
| 70,000 | 1.5 | 0.35 | 783 | 51 |

[1]crosslinker in poly(VAm);
[2]crosslinker in poly(AA); and
[3]Saline Flow Conductivity.

Multicomponent superabsorbent particles containing a low weight percent of a basic resin, as illustrated in Table 6, exhibit an excellent SFC and AUL, and further provide the advantage of substantial cost savings. The properties exhibited in Table 6 are unexpected, and it is theorized, but not relied on herein, that the unexpected performance is attributed to the polyelectrolyte effect of the poly(vinylamine). Similarly, other basic resins expected to exhibit such a polyelectrolyte effect include, but is not limited to, poly(diallylamine), poly(allylamine), poly(dimethyl diallylamine), polyethyleneimine, and polyazetidine.

In particular, multicomponent superabsorbent particles containing a relatively low weight percent of poly(allylamine), i.e., poly(AAm), were prepared and tested for AUL and AUNL. The test results are summarized in Table 8.

TABLE 8

| Wt % Poly(AAm)[1] | Mole % EGDGE[2] in Poly(AAm) | MOle % MBA[3] in Poly(AA) | AUNL | 4 hour AUL (g/g) 0.28 psi | 4 hour AUL (g/g) 0.7 psi |
|---|---|---|---|---|---|
| 30 | 0.75 | 0.35 | 61.7 | 49.8 | 45.6 |
| 35 | 0.5 | 0.35 | 65.2 | 53.5 | 50.9 |

[1]wt % of poly(AAm) in the multicomponent superabsorbent particle;
[2]crosslinker in poly(AAm); and
[3]crosslinker in poly(AA).

The results in Table 8 show that a multicomponent superabsorbent particle containing a low weight percent of poly(allylamine) can exhibit an AUL of greater than 50 g/g, and thereby provide an excellent SAP for use in articles of manufacture, such as diaper and catamenial devices.

In another series of tests, the ratio of acidic water-absorbing resin to basic water-absorbing resin in the multicomponent SAP particles was varied. In particular, Table 9 summarizes the AUNL data and the AUL data at different pressures for a series of multicomponent SAP particles containing a ratio of poly(vinylamine) to poly(AA) over the range of 25/75 to 40/60, by weight. The multicomponent SAP particles used in this series of tests were prepared by coextrusion of the poly(vinylamine) and poly(AA) resin. All multicomponent SAP particles used in the test were surface crosslinked with 50 ppm EGDGE. The multicomponent SAP particles were tested for an ability to absorb and retain synthetic urine.

TABLE 9

| Weight Ratio Poly (vinylamine)/ Poly(AA) | AUL 0.28 psi (1 hr) | AUL 0.7 psi (1 hr) | AUNL (1 hr) | AUL 0.28 psi (3 hr) | AUL 0.7 psi (3 hr) | AUNL (3 hr) | AUL 0.28 psi (17 hr) | AUL 0.7 psi (17 hr) | AUNL (17 hr) |
|---|---|---|---|---|---|---|---|---|---|
| 25/75 | 41.3 | 36.6 | 53.6 | 41.2 | 36.6 | 54 | 39.1 | 33.3 | 52.3 |
| 30/70 | 46.3 | 42.2 | 58.7 | 46.4 | 42.8 | 59.6 | 43.1 | 38.7 | 58.4 |
| 35/65 | 43.6 | 38.5 | 54.4 | 44.2 | 39.5 | 54.8 | 42 | 35.8 | 54.3 |
| 40/60 | 52.1 | 44.3 | 63.9 | 53.7 | 46.5 | 66.7 | 51.7 | 43.2 | 65.2 |

In addition to an ability to absorb and retain relatively large amounts of a liquid, it also is important for an SAP to exhibit good permeability, and, therefore, rapidly absorb the liquid. Therefore, in addition to absorbent capacity, or gel volume, useful SAP particles also have a high gel strength, i.e., the particles do not deform after absorbing a liquid. In addition, the permeability or flow conductivity of a hydrogel formed when SAP particles swell, or have already swelled, in the presence of a liquid is extremely important property for practical use of the SAP particles. Differences in permeability or flow conductivity of the absorbent polymer can directly impact on the ability of an absorbent article to acquire and distribute body fluids.

Many types of SAP particles exhibit gel blocking. "Gel blocking" occurs when the SAP particles are wetted and swell, which inhibits fluid transmission to the interior of the SAP particles and between absorbent SAP particles. Wetting of the interior of the SAP particles or the absorbent structure as a whole, therefore, takes place via a very slow diffusion process, possibly requiring up to 16 hours for complete fluid absorption. In practical terms, this means that acquisition of a fluid by the SAP particles, and, accordingly, the absorbent structure, such as a diaper, can be much slower than the rate at which fluids are discharged, especially in gush situations. Leakage from an absorbent structure, therefore, can occur well before the SAP particles in the absorbent structure are fully saturated, or before the fluid can diffuse or wick past the "gel blocked" particles into the remainder of the absorbent structure. Gel blocking can be a particularly acute problem if the SAP particles lack adequate gel strength, and deform or spread under stress after the SAP particles swell with absorbed fluid.

Accordingly, an SAP particle can have a satisfactory AUL value, but will have inadequate permeability or flow conductivity to be useful at high concentrations in absorbent structures. In order to have a high AUL value, it is only necessary that the hydrogel formed from the SAP particles has a minimal permeability such that, under a confining pressure of 0.3 psi, gel blocking does not occur to any significant degree. The degree of permeability needed to simply avoid gel blocking is much less than the permeability needed to provide good fluid transport properties. Therefore, SAPs that avoid gel blocking and have a satisfactory AUL value can still be greatly deficient in these other fluid handling properties.

An important characteristic of the multicomponent SAP particles of the present invention is permeability when swollen with a liquid to form a hydrogel zone or layer, as defined by the Saline Flow Conductivity (SFC) value of the SAP particles. SFC measures the ability of an SAP to transport saline fluids, such as the ability of the hydrogel layer formed from the swollen SAP to transport body fluids. A material having relatively high SFC value is an air-laid web of woodpulp fibers. Typically, an air-laid web of pulp fibers (e.g., having a density of 0.15 g/cc) exhibits an SFC value of about $200\times10^{7}$ $cm^{3}sec/g$. In contrast, typical hydrogel-forming SAPs exhibit SFC values of $1\times10^{-7}$ $cm^{3}sec/g$ or less. When an SAP is present at high concentrations in an absorbent structure, and then swells to form a hydrogel under usage pressures, the boundaries of the hydrogel come into contact, and interstitial voids in this high SAP concentration region become generally bounded by hydrogel. When this occurs, the permeability or saline flow conductivity properties in this region is generally indicative of the permeability or saline flow conductivity properties of a hydrogel zone formed from the SAP alone. Increasing the permeability of these swollen high concentration regions to levels that approach or even exceed conventional acquisition/distribution materials, such as wood pulp fluff, can provide superior fluid handling properties for the absorbent structure, thus decreasing incidents of leakage, especially at high fluid loadings.

Accordingly, it would be highly desirable to provide SAP particles having an SFC value that approaches or exceeds the SFC value of an air-laid web of wood pulp fibers. This is particularly true if high, localized concentrations of SAP particles are to be effectively used in an absorbent structure. High SFC values also indicate an ability of the resultant hydrogel to absorb and retain body fluids under normal usage conditions. A method for determining the SFC value of SAP particles is set forth in Goldman et al. U.S. Pat. No. 5,599,335, incorporated herein by reference.

A multicomponent SAP particle of the present invention, therefore, has an initial PUP capacity rate of at least 50 $g/g/hr^{1/2}$, and preferably at least 70 $g/g/hr^{1/2}$. To achieve the full advantage of the present invention, the multicomponent SAP particle has an initial PUP capacity rate of greater than 90 $g/g/hr^{1/2}$, and preferably greater than 100 $g/g/hr^{1/2}$.

In another test, the free swell rate (FSR) of a present multicomponent SAP particle was compared to the FSR of a standard poly(AA) SAP and 55/45 weight ratio of a poly(vinylamine)/poly(acrylic acid) dry particle blend. The FSR test, also known as a lockup test, is well known to persons skilled in the art.

The present multicomponent SAP particles had an FSR (in g/g/sec) of 0.49 and 0.48, for 55/45 weight ratio multicomponent SAP particles made in a KitchenAid mixer and a Brabender extruder, respectively. In comparison, a dry blend had an FSR of 0.10 and a standard neutralized poly(AA) had an FSR of 0.32. Multicomponent SAP particles of the present invention, therefore, have an FSR of greater than 0.35, preferably greater than 0.40, and most preferably greater than 0.45. These data further show the improved ability of the present SAP particles to absorb and retain larger amounts of an electrolyte-containing liquid quickly.

The multicomponent SAP particles also can be mixed with particles of a second water-absorbing resin to provide an SAP material having improved absorption properties. The second water-absorbing resin can be an acidic water-absorbing resin, a basic water-absorbing resin, or a mixture thereof. The SAP material comprises about 10% to about 90%, and preferably about 25% to about 85%, by weight, multicomponent SAP particles and about 10% to about 90%, and preferably, about 25% to about 85%, by weight, particles of the second water-absorbing resin. More preferably, the SAP material contains about 30% to about 75%, by weight, multicomponent SAP particles. To achieve the full advantage of the present invention, the SAP material contains about 35% to about 75%, by weight, the multicomponent SAP particles. The multicomponent SAP particles can be prepared by any of the previously described methods, e.g., extrusion, agglomeration, or interpenetrating polymer network, and can be of any shape, e.g., granular, fiber, powder, or platelets.

The second water-absorbing resin can be any of the previously discussed acidic resins used in the preparation of a multicomponent SAP. The second water-absorbing resin, either acidic or basic, can be un-neutralized (DN=0), partially neutralized ($0<DN<100$), or completely neutralized (DN=100). A preferred acidic water-absorbing resin used as the second resin is polyacrylic acid, preferably partially neutralized polyacrylic acid, e.g., DN about 50%, and preferably about 70% up to about 100%. The second water-absorbing resin also can be any of the previously discussed basic resins used in the preparation of a multicomponent SAP. Preferred basic water-absorbing resins used as the second resin are poly(vinylamine) or a poly (dialkylaminoalkyl(meth)acrylamide. Blends of acidic resins, or blends of basic resins, can be used as the second water-absorbing resin. Blends of an acidic resin and a basic resin also can be used as the second water-absorbing resin.

To illustrate the improved absorption properties demonstrated by an SAP material comprising multicomponent SAP particles and particles of a second water-absorbing resin, mixtures of multicomponent SAP particles and partially neutralized (DN=70) polyacrylic acid (poly(AA)) particles were prepared. As used here and throughout the specification poly(AA)(DN=70) refers to a standard, commercial poly(AA) neutralized about 70% to about 80%, and poly (AA)(DN=0) refers to un-neutralized poly(AA). The multicomponent SAP particles contain microdomains of poly (vinylamine) dispersed in poly(AA) (DN=0). The poly (vinylamine)/poly(AA) weight ratio of the multicomponent SAP particles was 70/30. The resulting SAP material was tested for an ability to absorb synthetic urine under load at 0.7 psi, in accordance with the previously described method. The results are summarized below:

| wt ratio[1)] | AUL 0.7 psi (1 hr.) | AUL 0.7 psi (3 hr.) | SFC ($\times 10^{-7}$ $cm^3$ sec/g) |
|---|---|---|---|
| 100/0 | 27.0 | 26.9 | 90 |
| 75/25 | 27.8 | 28.3 | 146 |
| 50/50 | 29.4 | 29.9 | 203 |
| 25/75 | 31.5 | 32.5 | 282 |
| 0/100 | 32.4 | 35.1 | 487 |

[1)]weight ratio of partially neutralized poly(AA) particles to multicomponent SAP particles.

The data presented above shows a substantial improvement in absorption properties achieved by an SAP material comprising a blend of multicomponent SAP particles and particles of a second water-absorbing resin over conventional, partially neutralized poly(AA).

An SAP material comprising a blend of multicomponent SAP particles and particles of a second water-absorbing resin outperformed a standard poly(AA) absorbent resin and a dry blend of water-absorbing resins. The blend of multicomponent SAP particles and particles of a second water-absorbing resin also performed well compared to an absorbent containing 100% multicomponent SAP particles.

A significant improvement in liquid absorption, both with respect to kinetics and retention, are expected if the standard poly(AA)(DN=70) presently used in diaper cores is completely replaced by multicomponent SAP particles, or is replaced by a superabsorbent material of the present invention, i.e., a composition containing multicomponent SAP particles and a second water-absorbing resin, such as poly(AA)(DN=70).

The improved results demonstrated by a diaper core containing the multicomponent SAP particles of the present invention also permit the thickness of the core to be reduced. Typically, cores contain 50% or more fluff or pulp to achieve rapid liquid absorption while avoiding problems like gel blocking. Cores which contain multicomponent SAP particles acquire liquids sufficiently fast to avoid problems, like gel blocking, and, therefore, the amount of fluff or pulp in the core can be reduced, or eliminated. A reduction in the amount of the low-density fluff results in a thinner core, and, accordingly, a thinner diaper.

Therefore, a core of the present invention can contain at least 50% of an SAP, preferably at least 75% of an SAP, and up to 100% of an SAP. In various embodiments, the presence of a fluff or pulp is no longer necessary, or desired. In each case, the SAP in a present core contains multicomponent SAP particles, in an amount of about 15% to 100% of the SAP. The remaining SAP can be a second water-absorbing resin, either basic or acidic. The second water-absorbing resin preferably is not neutralized, but can have a degree of neutralization up to 100%. The multicomponent SAP particles can be admixed with particles of a second water-absorbing resin for introduction into a diaper core. Alternatively, the diaper core can contain zones of multicomponent SAP particles and zones of a second water-absorbing resin.

In addition to a thinner diaper, the present cores also allow an acquisition layer to be omitted from the diaper. The acquisition layer in a diaper typically is a nonwoven or fibrous material, typically having a high degree of void space of "loft," that assists in the initial absorption of a liquid. Cores containing multicomponent SAP particles acquire liquid at a sufficient rate such that diapers free of an acquisition layer are practicable.

In summary, multicomponent SAP particles of the present invention contain a relatively low weight percent of a basic resin, and substantially outperform conventional SAP particles, e.g., partially neutralized poly(acrylic acid). The performance of present multicomponent SAP particles does not match the performance of multicomponent SAP particles containing greater than 40 weight % basic resin because deionization of the insult solution, e.g., urine, is less for a present multicomponent SAP particle. However, the polyelectrolyte effect of the basic resin offsets such lesser deionization, while maintaining performance far superior to that of a conventional SAP, as well as exhibiting an improved performance beyond that expected for such a particle. For example, it is unexpected that a 0.7 psi AUL (for synthetic urine) of greater than 50 g/g could be achieved using a multicomponent SAP particle containing less than 50 wt % poly(VAm).

Poly(vinylamine) works exceptionally well in a present multicomponent SAP because its optimum polyelectrolyte effect is predominant only at 50% neutralization. This effect is attributed to proton bridges between two amine functionalities to form a ring-like hydrogen bonded structure.

In addition, significant cost savings are achieved by the present multicomponent SAP particles because the amount of expensive basic resin in the particles is reduced, and the amount of expensive crosslinker can be reduced. For example, a 55/45 poly(VAm)/poly(AA) particle has an EGDGE content of 4 mole percent in the poly(VAm), whereas the 30/70 poly(VAm)/poly(AA) has an EGDGE content of 1.5 mole percent in the poly(VAm). These cost savings are achieved with a minimum reduction in optimum performance, while maintaining a significant performance increase over conventional SAP products.

Many modifications and variations of the invention as hereinbefore set forth can be made without departing from the spirit and scope thereof and, therefore, only such limitations should be imposed as are indicated by the appended claims.

What is claimed is:

1. A multicomponent superabsorsent particle comprising, in a single particle, about 20% to about 40%, by weight, of one or more microdomains of at least one basic water-absorbing resin in contact with about 60% to about 80%, by weight, of one or more microdomain of at least one acidic water-absorbing resin.

2. The particle of claim 1 comprising a plurality of microdomains of at least one basic water-absorbing resin and a plurality of microdomains of at least one acidic water-absorbing resin.

3. The particle of claim 1 wherein the basic resin comprises a strong basic resin, and the acidic resin comprises a strong acidic resin, a weak acidic resin, or a mixture thereof.

4. The particle of claim 1 wherein the basic resin comprises a weak basic resin, and the acidic resin comprises a strong acidic resin, a weak acidic resin, or a mixture thereof.

5. The particle of claim 1 having a weight ratio of acidic resin to basic resin of about 75:25 to about 65:35.

6. The particle of claim 1 having a weight ratio of acidic resin to basic resin of about 70:30 to about 60:40.

7. The particle of claim 1 having a mole ratio of basic resin to acidic resin of about 0.5:1 to about 1:1.

8. The particle of claim 1 having a mole ratio of basic resin to acidic resin of about 0.6:1 to about 0.8:1.

9. The particle of claim 1 containing about 50% to 100%, by weight, of basic resin plus acidic resin.

10. The particle of claim 1 wherein the particle is annealed at a temperature of about 60° C. to about 200° C. for about 20 to about 120 minutes.

11. The particle of claim 1 wherein the particle is surface crosslinked with up to about 10,000 ppm of a surface crosslinking agent.

12. The particle of claim 11 wherein the surface crosslinking agent is selected from the group consisting of a polyhydroxy compound, a metal salt, a quaternary ammonium compound, a β-hydroxyalkylamide, a multifunctional epoxy compound, an alkylene carbonate, a polyaziridine, a haloepoxy, a polyamine, a polyisocyanate, and mixtures thereof.

13. The particle of claim 1 wherein the basic resin is lightly crosslinked and has about 75% to 100% basic moieties present in a free base form.

14. The particle of claim 1 wherein at least 6% of the monomer units comprising the basic resin are basic monomer units.

15. The particle of claim 1 wherein the basic resin is selected from the group consisting of a poly(vinylamine), a polyethylenimine, a poly(allylguanidine), a poly(allylamine), a poly(diallylamine), polyazetidine, and mixtures thereof.

16. The particle of claim 1 wherein the acidic resin contains a plurality of carboxylic acid, sulfonic acid, sulfuric acid, phosphonic acid, or phosphoric acid groups, or a mixture thereof.

17. The particle of claim 1 wherein the acidic resin is lightly crosslinked and has about 75% to 100% acid moieties present in the free acid form.

18. The particle of claim 1 wherein at least 10% of the monomer units comprising the acidic resin are acidic monomer units.

19. The particle of claim 1 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly(vinylsulfonic acid), a poly(vinylphosphoric acid), a poly(vinylsulfuric acid), a sulfonated polystyrene, a poly(aspartic acid), a poly(lactic acid), and mixtures thereof.

20. The particle of claim 1 wherein the basic resin comprises a poly(vinylamine), a poly(vinylguanidine), a polyethylenimine, or a mixture thereof, and the acidic resin comprises poly(acrylic acid).

21. The particle of claim 1 further comprising at least one microdomain of a matrix resin in an amount of 0% to 50% by weight of the particle.

22. The particle of claim 1 consisting essentially of microdomains of the acidic resin and the basic resin.

23. An article comprising a multicomponent superabsorbent particle of claim 1.

24. A method of absorbing an aqueous medium comprising contacting the medium with a plurality of particles of claim 1.

25. A method of claim 24 wherein the aqueous medium contains electrolytes.

26. A method of claim 25 wherein the electrolyte-containing aqueous medium is selected from the group consisting of urine, saline, menses, and blood.

27. The particle of claim 1 in the form of a bead, a granule, a flake, an interpenetrating polymer network, a fiber, an agglomerated particle, a laminate, a powder, a foam, or a sheet.

28. The particle of claim 1 having an absorption under load at 0.7 psi of at least about 10 grams of 0.9% saline per gram of particles, after one hour, and at least about 10 grams of 0.9% saline per gram of particles after three hours.

29. The particle of claim 1 having a saline flow conductivity value of at least $150\times10^{-7}$ $cm^3sec/g$.

30. The particle of claim 1 having an initial performance under pressure capacity rate of greater than 50 $g/g/hr^{1/2}$.

31. The particle of claim 1 having a free swell rate greater than 0.35 g/g/sec.

32. A superabsorbent material comprising:

(a) multicomponent superabsorbent particles of claim 1, and (b) particles of a second water-absorbing resin selected form the group consisting of an acidic water-absorbing resin, a basic water-absorbing resin, and mixtures thereof.

33. The superabsorbent material of claim 32 wherein the multicomponent superabsorbent particles are present in an amount of about 10% to about 90%, by weight, of the material.

34. The superabsorbent material of claim 32 wherein the multicomponent superabsorbent particles are 0% to 25% neutralized, and the second water-absorbing resin is 0% to 100% neutralized.

35. The superabsorbent material of claim 32 wherein the second water-absorbing resin has a degree of neutralization from 0 to 70.

36. The superabsorbent material of claim 32 wherein the second water-absorbing resin comprises an acidic water-absorbing resin.

37. The superabsorbent material of claim 32 wherein the second water-absorbing resin comprises a basic water-absorbing resin.

38. A method of absorbing an aqueous medium comprising contacting the medium with a superabsorbent material of claim 32.

39. An article comprising a core containing a superabsorbent material of claim 32, said core comprising about 1% to 100% by weight of the superabsorbent material.

* * * * *

UNITED STATES PATENT AND TRADEMARK OFFICE

CERTIFICATE OF CORRECTION

PATENT NO. : 6,590,137 B2
DATED : July 8, 2003
INVENTOR(S) : Michael A. Mitchell et al.

It is certified that error appears in the above-identified patent and that said Letters Patent is hereby corrected as shown below:

Column 34,
Line 66, "superaborsent" should be -- superabsorbent --

Column 36,
Line 40, "form the group" should be -- from the group --

Signed and Sealed this

Third Day of February, 2004

JON W. DUDAS
*Acting Director of the United States Patent and Trademark Office*